United States Patent
Makarczyk et al.

(10) Patent No.: US 12,428,364 B2
(45) Date of Patent: Sep. 30, 2025

(54) METHOD FOR PROCESSING BENZENE POLYCARBOXYLIC ACID ESTERS AND USE OF SAME TO PRODUCE CYCLOHEXANE POLYCARBOXYLIC ACID ESTERS

(71) Applicant: BASF SE, Ludwigshafen am Rhein (DE)

(72) Inventors: Piotr Makarczyk, Ludwigshafen am Rhein (DE); Boris Breitscheidel, Ludwigshafen am Rhein (DE); Zsolt Szarka, Ludwigshafen am Rhein (DE); Sonja Judat, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 1069 days.

(21) Appl. No.: 17/433,700

(22) PCT Filed: Feb. 21, 2020

(86) PCT No.: PCT/EP2020/054583
§ 371 (c)(1),
(2) Date: Apr. 28, 2022

(87) PCT Pub. No.: WO2020/173818
PCT Pub. Date: Sep. 3, 2020

(65) Prior Publication Data
US 2022/0177405 A1 Jun. 9, 2022

(30) Foreign Application Priority Data
Feb. 25, 2019 (EP) .................................... 19159145

(51) Int. Cl.
*C07C 67/303* (2006.01)
*C07C 67/54* (2006.01)

(52) U.S. Cl.
CPC ............ *C07C 67/303* (2013.01); *C07C 67/54* (2013.01)

(58) Field of Classification Search
None
See application file for complete search history.

(56) References Cited

U.S. PATENT DOCUMENTS 3,091,628 A 5/1963 Simpson
3,203,998 A 8/1965 Honse
(Continued)

FOREIGN PATENT DOCUMENTS

DE 2823165 A1 11/1979
DE 4228887 A1 3/1994
(Continued)

OTHER PUBLICATIONS

International Preliminary Report on Patentability (Chapter II) received for PCT Patent Application No. PCT/EP2020/054583, mailed on Jan. 22, 2021, 19 pages (6 pages of English Translation and 13 pages of Original Document).

(Continued)

*Primary Examiner* — Amy C Bonaparte
(74) *Attorney, Agent, or Firm* — Faegre Drinker Biddle & Reath LLP

(57) ABSTRACT

The present invention relates to a process for purifying benzenepolycarboxylic esters and for preparing cyclohexanepolycarboxylic esters by hydrogenating the purified benzenepolycarboxylic esters. The invention further relates to benzenepolycarboxylic esters and cyclohexanepolycarboxylic esters having a small proportion of by-products, especially of dialkyl ethers, and especially to diisononyl cyclohexane-1,2-dicarboxylate having a small proportion of diisononyl ether. The invention also relates to the use of the cyclohexanepolycarboxylic esters as plasticizers, especially (Continued)

in products intended for human contact, such as children's toys, food packaging and medical articles.

25 Claims, 5 Drawing Sheets

(56) References Cited

U.S. PATENT DOCUMENTS

| | | | |
|---|---|---|---|
| 5,136,108 | A | 8/1992 | Gaffney et al. |
| 5,349,097 | A | 9/1994 | Thome et al. |
| 5,463,143 | A | 10/1995 | Singleton et al. |
| 7,893,295 | B2 | 2/2011 | Schlosberg et al. |

FOREIGN PATENT DOCUMENTS

| | | |
|---|---|---|
| DE | 4431528 A1 | 3/1996 |
| DE | 19604791 A1 | 8/1997 |
| DE | 19624484 A1 | 1/1998 |
| DE | 19624485 A1 | 1/1998 |
| DE | 10146847 A1 | 4/2003 |
| DE | 10251311 A1 | 5/2003 |
| DE | 10225565 A1 | 12/2003 |
| EP | 0005737 A1 | 12/1979 |
| EP | 0271092 A1 | 6/1988 |
| EP | 0394842 A1 | 10/1990 |
| EP | 0643031 A1 | 3/1995 |
| EP | 0759558 A2 | 2/1997 |
| EP | 0814098 A2 | 12/1997 |
| EP | 3214067 A1 | 9/2017 |
| GB | 0721540 A | 1/1955 |
| GB | 0879803 A | 10/1961 |
| GB | 1165309 A | 9/1969 |
| GB | 1302146 A | 1/1973 |
| GB | 1320188 A | 6/1973 |
| JP | 2000-319444 A | 11/2000 |
| RU | 2059597 C1 | 5/1996 |
| WO | 92/13818 A1 | 8/1992 |
| WO | 93/24644 A1 | 12/1993 |
| WO | 95/14647 A1 | 6/1995 |
| WO | 98/03462 A1 | 1/1998 |
| WO | 99/32427 A1 | 7/1999 |
| WO | 2003/066642 A1 | 8/2003 |
| WO | 2004/009526 A1 | 1/2004 |
| WO | 2004/046078 A1 | 6/2004 |
| WO | 2010/076192 A1 | 7/2010 |
| WO | 2011/082991 A2 | 7/2011 |
| WO | 2014/053618 A1 | 4/2014 |

OTHER PUBLICATIONS

International Search Report and Written Opinion received for PCT Patent Application No. PCT/EP2020/054583, mailed on May 7, 2020, 11 pages (2 pages of English Translation and 9 pages of Original Document).

METHOD FOR PROCESSING BENZENE POLYCARBOXYLIC ACID ESTERS AND USE OF SAME TO PRODUCE CYCLOHEXANE POLYCARBOXYLIC ACID ESTERS

CROSS-REFERENCE TO RELATED APPLICATIONS

This application is a national stage application (under 35 U.S.C. § 371) of PCT/EP2020/054583, filed Feb. 21, 2020, which claims benefit of European Application No. 19159145.2, filed Feb. 25, 2019, both of which are incorporated herein by reference in their entirety.

BACKGROUND OF THE INVENTION

The present invention relates to a process for purifying benzenepolycarboxylic esters and for preparing cyclohexanepolycarboxylic esters by hydrogenating the purified benzenepolycarboxylic esters. The invention further relates to benzenepolycarboxylic esters and cyclohexanepolycarboxylic esters having a small proportion of by-products, especially of dialkyl ethers, and especially to diisononyl cyclohexane-1,2-dicarboxylate having a small proportion of diisononyl ethers. The invention also relates to the use of the cyclohexanepolycarboxylic esters as plasticizers, especially in products intended for human contact, such as children's toys, food packaging and medical articles.

STATE OF THE ART

While benzenepolycarboxylic esters were used in the past on a large scale as plasticizers in plastics, for example PVC, attempts are increasingly being made to replace them, since the phthalate plasticizers in particular are suspected of being harmful to health. This is particularly true of plastics that are used in sensitive fields of application, such as children's toys, food packaging or medical articles. Since cyclohexanepolycarboxylic esters, by contrast with their unhydrogenated aromatic analogs, are not of toxicological concern, they are of particularly good suitability as alternative plasticizers for these sensitive applications. Thus, benzenepolycarboxylic esters nowadays also serve as an important intermediate for preparation of cyclohexanepolycarboxylic esters. There is still in need for novel processes that enable the provision of cyclohexanepolycarboxylic esters having a low content of by-products, especially of comparatively nonvolatile by-products such as ethers.

In many cases, benzenepolycarboxylic esters are prepared in the form of a direct esterification of carboxylic acids with alcohols with elimination of water in the presence of an esterification catalyst. Suitable esterification catalysts are Brønsted acids, such as sulfuric acid, alpha-naphthalenesulfonic acid, phosphoric acid, methanesulfonic acid and toluenesulfonic acid, and Lewis acids such as alkoxides, carboxylates and chelate compounds of titanium, zirconium, tin, aluminum and zinc. When Brønsted acids are used as catalysts, there is an upper limit to the reaction temperature for the esterification. For instance, in the case of esterification with sulfuric acid, temperatures of more than 140° C. should generally not be exceeded in order to avoid discoloration of the product. In the individual case, it is possible to conduct the esterification at temperatures up to 165° C. in order to achieve acceptable product quality, although the acid-catalyzed dehydration of the alcohol increases as a side reaction. As well as esterification, with increasing temperatures, there is also formation of symmetric ethers, ultimately resulting in alkenes with elimination of water. When the temperature is increased to about 175° C. to 200° C., there is a considerable increase in the reaction rate, but it is not possible to avoid deteriorations in quality resulting from increased side reactions, for example ether formation. The use of neutral catalysts, for example of titanates or zirconates, has the advantage of lower alcohol breakdown and ether formation. Owing to the lower activity compared to the Brønsted acids, however, it is generally necessary to employ higher esterification temperatures of, for example, more than 180° C. These catalysts are therefore usually used in the preparation of the long-chain benzenepolycarboxylic esters. Owing to the high boiling points of the long-chain alcohols, it is possible to reach esterification temperatures of more than 200° C. without needing to perform the reaction under elevated pressure. For example, titanates of short-chain alcohols, such as titanium isopropoxide, react rapidly with free higher alcohols in a transesterification reaction to give the corresponding orthotitanates, for example with isononanol (trimethyl-3,3,5-hexanol) to give tetraisononyl titanate, with distillative removal of isopropanol released. The Lewis acid formed here transfers the isononanol radical, forming an ester with a carboxyl group of the carboxylic acid used, and reacts with free isononanol to give tetraisononyl titanate again. At higher temperatures of, for example, more than 200° C., even with neutral catalysts such as the titanates, there is an increase in the dehydration of the alcohol and the further side reactions, such as the formation of ethers and alkenes. Alternatively, benzenedicarboxylic esters can be prepared by reacting corresponding carboxylic anhydrides with alcohols. If the esterification has a two-stage configuration, at least at the first esterification stage for formation of the monoesters, it is possible to dispense with the use of an esterification catalyst.

It is known that lower-boiling impurities than the alcohol can be separated from the reaction mixture as early as in the course of esterification. WO 2010/076192 describes a process for preparing carboxylic esters by reacting a carboxylic acid or a carboxylic anhydride with an alcohol, wherein the water formed in the reaction is distilled off as an alcohol-water azeotrope with the vapor, the vapor is at least partly condensed, the condensate is separated into an aqueous phase and an organic phase, lower-boiling components than the alcohol (low boilers) are at least partly removed from the organic phase, and the organic phase depleted of low boilers is at least partly recycled into the reaction system. The low boilers are mainly olefins that are formed by elimination of water from the alcohol used. While the distillative removal and discharge of the low boilers from the alcohol recycle stream is possible for most alcohols, the secondary components that are of higher molecular weight and hence less volatile, such as the ethers, remain in the product as an impurity.

The crude esterification product obtained in the industrial scale preparation of benzenepolycarboxylic esters is typically subjected to multiple workup steps. These include the removal of excess alcohol, which is generally effected by evaporating, and of the catalyst used for esterification. Brønsted acid catalysts are neutralized by adding aqueous base, such as NaOH or KOH. Neutral catalysts such as titanium alkoxides, zirconium alkoxides, etc., are likewise hydrolyzed by addition of an aqueous basic solution, possibly with formation of sparingly soluble metal salts and/or metal alkoxides. The deactivated catalyst can be removed by extraction, in which case the crude esterification product treated with the aqueous base is left to stand until it separates into two phases through mechanical settling (an aqueous phase comprising at least some of the hydrolyzed catalyst and an organic phase comprising the majority of the esterification product) that can be drawn off separately. The organic phase obtained after the extractive separation is optionally neutralized by single or multiple washing with an acidic aqueous solution and/or with water. Solids formed in the hydrolysis of neutral catalysts can be separated from the liquid product phase, for example by means of sedimentation and/or filtration. The result is a neutral, alcohol-depleted crude ester which can be subjected at least to an additional purification step in order that the crude product is freed of residual moisture and residual alcohol. The low-boiling components such as water and alcohol are evaporated, while the nonvolatile ester product is obtained as bottoms discharge or residue. This workup step can be effected, for example, in a tank under reduced pressure, in a stripping apparatus by treatment with a stripping agent, such as steam or nitrogen, in a falling-film evaporator, thin-film evaporator, in a vacuum steam distillation column or the like. The benzenepolycarboxylic ester thus obtained can, if desired, be contacted with a solid adsorbent, such as charcoal, silica gel or clay minerals, for example in order to achieve a further improvement in color number.

H. Suter describes, in Phthalsäureanhydrid und seine Verwendung, Wissenschaftliche Forschungsberichte, Reihe II: Anwendungstechnik und angewandte Wissenschaft [Phthalic Anhydride and Its Use, Scientific Research Reports, Series II: Application Technology and Applied Science], Dr. Dietrich Steinkopf Verlag, Darmstadt, 1972, pages 79-80 and fig. 16, a BASF process for preparing phthaliate plasticizers, such as di-2-ethylhexyl phthalate (DOP), by esterifying phthalic anhydride with alcohol. A special feature of this process is that it runs autocatalytically, i.e. without addition of acids. The alcohol-depleted, neutralized crude ester, in an apparatus referred to as steam-stripping column, is subjected to a treatment with steam under reduced pressure to reduce the level of volatile components. The low-boiling water vapor and alcohol components are drawn off at the top of the column, while the stripped ester product is withdrawn continuously from the column as bottoms discharge. After the vapor has condensed, the aqueous phase is separated from the alcohol in a phase separator and the alcohol is returned to the synthesis. There is no description of the removal of further secondary components formed in the esterification, such as alkenes and ethers.

As mentioned at the outset, it is likewise known that benzenepolycarboxylic esters can be subjected to a hydrogenation by reaction with hydrogen in the presence of a hydrogenation catalyst in order to obtain the corresponding cyclohexanepolycarboxylic esters. For example, EP 0005737 A1 (DE-A 28 23 165) describes the hydrogenation of aromatic carboxylic esters over supported Ni, Ru, Rh or Pd catalysts to give the corresponding cycloaliphatic carboxylic esters at temperatures of 70 to 250° C. and pressures of 30 to 200 bar.

WO 99/32427 describes a process for hydrogenating benzenepolycarboxylic acids or derivatives thereof, for example the esters, using a catalyst having macropores. The process features a high space-time yield and high selectivity. This document likewise describes the use of the cyclohexanepolycarboxylic acid derivatives thus obtained as plasticizers in plastics. There is specific mention, for example, of diisononyl cyclohexane-1,2-dicarboxylate.

There have already been efforts to provide cyclohexanepolycarboxylic esters with a reduced content of particular by-products.

WO 2014/053618 describes a process for preparing cyclohexanepolycarboxylic acids or derivatives thereof with a small proportion of secondary components, especially of hexahydrophthalide and isononyl alcohol. This object is achieved by hydrogenating the corresponding benzenepolycarboxylic acids or derivatives thereof in the presence of a specific eggshell catalyst and at a superficial velocity of not more than 50 m/h.

EP 32140067 A1 relates to a process for purifying crude cyclohexanepolycarboxylic ester products as obtained in the hydrogenation of the corresponding benzenepolycarboxylic ester precursors, in which the thermal stress that acts on the benzenepolycarboxylic esters and the amount of the offgases and/or wastewaters (condensates) that are formed in the process and have to be sent to processing or waste disposal are minimized. This object is achieved by a process in which i) a cyclohexanepolycarboxylic ester-containing crude product is provided, ii) the crude product provided in step i) is subjected to thermal purification in at least one mass transfer apparatus by introduction of a gas stream G1 in the bottom of the at least one mass transfer apparatus to give a bottom product SP which is enriched in the cyclohexanepolycarboxylic ester and a gas stream AG1 which is enriched in at least one impurity, wherein the gas stream G1 comprises a gas or gas mixture which is not condensable under the process conditions and a maximum of 30% by weight of steam and wherein the gas stream AG1 is subjected to at least partial condensation of the impurities present therein to give a gas stream AG2 which is depleted impurities and is, optionally together with the remaining part of the gas stream AG1, reintroduced into the bottom of the mass transfer apparatus.

The processes for preparing cyclohexanepolycarboxylic esters that are known from the prior art and the esters thus obtained are still in need of improvement. For instance, the cyclohexanepolycarboxylic esters prepared with the aid of these processes still have an undesirably high proportion of by-products. It has been found that specifically the medium boilers that are formed in the esterification of the benzenepolycarboxylic esters and have a boiling point above the boiling point of water and the alcohol used for esterification and below the boiling point of the benzenepolycarboxylic esters and the cyclohexanepolycarboxylic esters are removed only inadequately to date and remain as secondary components in the product. This is especially true of the ethers formed from the alcohols used for esterification through nucleophilic substitution as a side reaction, for example diisononyl ether. The formation of ethers as by-product in the esterification can only be limited to a limited degree. According to the quality of the raw materials used and the process conditions, the content of ethers in the finished product may be up to several thousand ppm by weight. In addition, ethers can also be formed in the hydrogenation of the benzenepolycarboxylic esters to the cyclohexanepolycarboxylic esters. The effect of a high proportion of by-products can be that the cyclohexanepolycarboxylic esters prepared by prior art processes have disadvantageous performance properties when used as plasticizers, for example high volatility and/or poor compatibility with plastics, for example PVC. As a result, the cyclohexanepolycarboxylic esters known from the prior art are of less good suitability for sensitive applications in which the products produced from the plasticized plastics are intended for human contact, for example in children's toys, food packaging or medical articles.

Thus, there is still a need for a process that enables the preparation of cyclohexanepolycarboxylic esters with a small proportion of by-products, specifically of medium boilers, and especially of ethers. More particularly, it is an object of the present invention to provide a process for preparing diisononyl cyclohexane-1,2-dicarboxylate having a small content of diisononyl ether. The process is to be economically viable and efficient and is to avoid particularly complex purification steps and/or the loss of starting alcohol.

It has been found that, surprisingly, it is possible in the workup of the crude esters from the esterification of a benzenepolycarboxylic acid with at least one alcohol, by stripping the crude ester with a steam-containing gas stream, to at least partly remove the ethers formed as a by-product with the vapor from the ester product. It has additionally been found that it is possible, through the choice of suitable catalysts, to reduce or to avoid the formation of ethers in the hydrogenation of the benzenepolycarboxylic esters to give the cyclohexanepolycarboxylic esters.

SUMMARY OF THE INVENTION

The invention therefore firstly provides a process for workup of a crude ester from the esterification of a benzenepolycarboxylic acid with at least one $C_4$-$C_{12}$ monoalkanol, wherein the crude ester additionally comprises
 at least one di-($C_4$-$C_{12}$-alkyl) ether from the etherification of the at least one $C_4$-$C_{12}$ monoalkanol,
 optionally the at least one $C_4$-$C_{12}$ monoalkanol, and
 optionally water,
in which the crude ester is subjected to a thermal purification in at least one mass transfer apparatus by introducing a steam-containing gas stream in the region of the bottom of the mass transfer apparatus to obtain a bottom product enriched in the at least one benzenepolycarboxylic ester and depleted of the at least one di-($C_4$-$C_{12}$-alkyl) ether and a vapor enriched in the at least one di-($C_4$-$C_{12}$-alkyl) ether.

The invention further provides a composition comprising at least one benzenepolycarboxylic ester of the general formula (II)

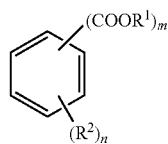

in which
 m is 2, 3 or 4,
 n is 0, 1, 2 or 3,
 $R^1$ is independently straight-chain or branched $C_4$-$C_{12}$-alkyl, and
 $R^2$ is independently straight-chain or branched $C_1$-$C_4$-alkyl,
and 1 to 500 ppm by weight, based on the total weight of the composition, of at least one ether of the general formula $R^1$—O—$R^1$.

The invention further provides a composition comprising diisononyl phthalate and 10 to 500 ppm by weight, based on the total weight of the composition, of diisononyl ether.

The invention further provides a composition comprising at least one cyclohexanepolycarboxylic ester of the general formula (I)

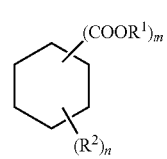

in which
 m is 2, 3 or 4,
 n is 0, 1, 2 or 3,
 $R^1$ is independently straight-chain or branched $C_4$-$C_{12}$-alkyl, and
 $R^2$ is independently straight-chain or branched $C_1$-$C_4$-alkyl,
and 1 to 1000 ppm by weight, based on the total weight of the composition, of at least one ether of the general formula $R^1$—O—$R^1$.

The invention further provides a composition comprising diisononyl cyclohexane-1,2-dicarboxylate and 10 to 1000 ppm by weight, based on the total weight of the composition, of diisononyl ether.

The invention further provides for the use of a composition as defined above and hereinafter as plasticizer, preferably as plasticizer for polyvinylchloride.

The invention further provides for use of a composition as defined above and hereinafter in products intended for human contact, preferably in children's toys, food packaging or in medical articles.

DESCRIPTION OF THE INVENTION

The ester of the benzenepolycarboxylic acid with at least one $C_4$-$C_{12}$ monoalkanol is also referred to hereinafter as "benzenepolycarboxylic ester" for short. Correspondingly, the ester of the cyclohexanepolycarboxylic acid with at least one $C_4$-$C_{12}$ monoalkanol is also referred to as "cyclohexanepolycarboxylic ester" for short.

The crude ester used for workup in the process of the invention is a composition comprising components having different boiling points. The crude ester as high boiler comprises at least one benzenepolycarboxylic ester with at least one $C_4$-$C_{12}$ monoalkanol. Low-boiling components are the $C_4$-$C_{12}$ monoalkanols, water and $C_4$-$C_{12}$-alkenes. Medium-boiling components having a boiling point between the high boilers and the low boilers are the di-($C_4$-$C_{12}$-alkyl) ethers.

The crude ester used for workup preferably comprises
 91% to 99.8% by weight of at least one ester of a benzenepolycarboxylic acid with at least one $C_4$-$C_{12}$ monoalkanol,
 0.05% to 1% by weight of at least one di-($C_4$-$C_{12}$-alkyl) ether,
 0.1% to 5% by weight of at least one $C_4$-$C_{12}$ monoalkanol, and
 0.05% to 3% by weight of water.

Preferred benzenepolycarboxylic esters that are suitable for use in the process of the invention for workup of a crude ester are the compounds of the general formula (II) defined in detail above and hereinafter, to which reference is made in full.

Workup of a Crude Ester of the Benzenepolycarboxylic Acid

In the process of the invention, a benzenepolycarboxylic ester-containing crude product is subjected to a thermal purification in at least one mass transfer apparatus by introducing a steam-containing gas stream in the region of the bottom of the mass transfer apparatus. Such a thermal purification is also referred to hereinafter as "stripping". In general, the term "stripping" is understood to mean a process known to the person skilled in the art in which a crude product comprising evaporable impurities is contacted in a suitable mass transfer apparatus with a gaseous stripping medium, also called "stripping gas", that takes up at least some of the impurity. Specifically, the thermal purification in the at least one mass transfer apparatus is effected under reduced pressure.

The workup of a crude ester by the process of the invention is preferably effected continuously. This means that crude ester is fed continuously into the mass transfer apparatus, a steam-containing gas stream is introduced and a vapor stream is discharged. Independently thereof, the removal of at least a portion of the di-($C_4$-$C_{12}$-alkyl) ether from the vapor stream and/or the recycling of at least a portion of the condensed vapor into the mass transfer may be discontinuous or continuous. The latter is described in detail hereinafter.

According to the invention, a steam-containing gas stream as stripping gas is introduced into the mass transfer apparatus. This gas stream preferably comprises at least 50% by volume, more preferably at least 70% by volume and especially at least 90% by volume of steam. If desired, the gas stream introduced into the mass transfer apparatus may additionally comprise at least one gas which is uncondensable under the process conditions. The uncondensable gas is preferably selected from nitrogen, carbon dioxide, oxygen, hydrogen, helium, neon, argon and mixtures thereof. More particularly, the gas stream introduced into the mass transfer apparatus consists solely of steam.

In the context of the present invention, the term "thermal purification" is understood to mean a process known to the person skilled in the art in which a mixture of matter is separated by supply of a gas and optionally additionally by supply of thermal energy. In principle, the supply of thermal energy brings about the separation of a mixture of matter on account of the different boiling points of the compounds present in the mixture of matter. The separation is then especially a distillative separation. By virtue of the supply of a gas to the mixture of matter, the separation is effected essentially via the different volatility of the individual compounds present in the mixture of matter.

Volatile compounds, i.e. compounds that can be more easily converted to the gas phase, are more likely to be entrained here than nonvolatile compounds, i.e. compounds that can be converted to the gas phase only with difficulty. Preferably, in the thermal purification of the crude ester by the process of the invention, the mixture to be separated is separated both by the introduction of a stripping gas and by supply of thermal energy.

The heat is supplied predominantly via the benzenepolycarboxylic ester-containing crude product fed in. Furthermore, heat can additionally be supplied via the steam-containing gas stream (i.e. the stripping gas) and/or the column bottom can be heated by means of bottom heating.

In the context of the present invention, the term "mass transfer apparatus" is understood to mean an apparatus in which gases and liquids are contacted with one another and mass transfer between the gas or gas phase and the liquid or liquid phase is enabled (mass transfer from the gas or gas phase into the liquid or liquid phase and/or from the liquid or liquid phase into the gas or gas phase).

In the present process, the mass transfer apparatus is generally an apparatus that enables the passage of volatile constituents present in the liquid or liquid phase to the gas or gas phase.

Suitable mass transfer apparatuses are generally all apparatuses familiar to the person skilled in the art for separation of reaction mixtures comprising liquid components. Suitable apparatuses comprise columns that may be equipped with internals and/or with packings, bubble columns, spinning band column evaporators, thin-film evaporators, falling-film evaporators, forced circulation evaporators, Sambay evaporators, spray apparatuses, etc., and combinations thereof. In a specific configuration, the mass transfer apparatus used is a single column.

Preferably, at least one column is used for thermal purification of the crude ester, especially a stripping distillation column or an arrangement of columns comprising at least one stripping distillation column. In a specific configuration, the purification is effected in a single stripping distillation column. More preferably, thermal purification of the crude ester is accomplished using at least one column equipped with internals, for example with trays, such as bubble-cap trays or sieve trays, or with plates, such as sieve plates, and/or with packings, for example with random packings (e.g. Pall rings, IMTP random packings or other high-performance random packings) or structured packings (e.g. Mellapak Plus™). Suitable configurations of distillation apparatuses suitable for thermal purification can be found, for example, in Green, Don W.; Perry, Robert H. (2008), Perry's Chemical Engineers Handbook (8th Edition) McGraw-Hill, Section 14.

Thermal purification of the crude ester is more preferably accomplished using at least one packed column. This specifically has low-pressure-drop internals and/or packings, such as high-performance structured packings in particular.

In a specific configuration of the process of the invention, thermal purification of the crude ester is accomplished using at least one column, wherein the crude ester is fed in in the side region of the column. The "side region of the column" in the context of the present invention is understood to mean a region beneath the top region and above the bottom. In general, there are separating internals below the feed for the crude ester. There are preferably separating internals below and above the feed for the crude ester. The region above the feed is also referred to as "rectifying section" and the region below the feed as "stripping section". In the context of the invention, rather than a stripping section, it is also possible to provide an analogous apparatus, for example an external forced circulation evaporator. In the context of the present invention, the "top region of the column" is understood to mean the upper region of the column present above the feed for the crude ester and, if present, above the separating column internals. Correspondingly, the "bottom region of the column" refers to the region at the bottom end of the column which is below the separating column internals and comprises the liquid bottom product.

In a specific embodiment, thermal purification of the crude ester is accomplished using at least one column having
  a side feed for the crude ester,
  a rectifying section above the feed point for the crude ester,
  a reflux feed for at least a portion of the condensed vapor above the rectifying section,
  a feed for the steam-containing gas stream in the region of the bottom of the column.

This specific embodiment is particularly suitable for variants 2 and 3 described hereinafter.

Preferably, the rectifying section above the feed point for the crude ester has 0 to 10 theoretical plates, more preferably 0 to 5 theoretical plates, especially 0 to 2 theoretical plates.

The at least one column used for thermal purification of the crude ester may comprise further internals. These include, for example, liquid distributors. These are preferably present below the reflux feed for at least a portion of the condensed vapor and/or below the feed point for the crude ester. These further include liquid collectors. These are preferably present below or within the rectifying section. Liquid collectors serve for redistribution and/or at least partial discharge of the collected liquids.

The vapor obtained in the inventive workup of the crude ester is drawn off at the top of the mass transfer apparatus. If thermal purification of the crude ester is accomplished using a column, the vapor is drawn off at the top of the column.

Partial or complete condensation of the vapor can be accomplished using all suitable condensers. These can be cooled with any desired cooling media. Condensers with air cooling and/or water cooling are preferred, and air cooling is particularly preferred.

The condensed vapor may be subjected to a phase separation into an aqueous phase and an organic phase. For this purpose, the condensate is typically passed into a phase separator (decanter), where it divides into two phases as a result of mechanical settling, and these can be drawn off separately. The aqueous phase is removed and, optionally after workup, can be discarded or used for production of steam for stripping of the crude ester. The condensed vapor may be partly or fully discharged or partly or fully subjected to a further utilization as described hereinafter.

If the vapor comprises lower-boiling components than the $C_4$-$C_{12}$ monoalkanol, specifically $C_4$-$C_{12}$ alkenes that cannot be condensed with acceptable expenditure in one stage with $C_4$-$C_{12}$ monoalkanol and di-($C_4$-$C_{12}$-alkyl) ether or the enrichment of which in the condensed vapor is undesirable, these can be separated off as gas phase and recondensed or discharged.

It has been found that, surprisingly, it is possible by the process of the invention to workup the crude ester to obtain a bottom product depleted of di-($C_4$-$C_{12}$-alkyl) ether and enriched in benzenepolycarboxylic ester, and a vapor enriched in di-($C_4$-$C_{12}$-alkyl) ether. The content in the vapor of di-($C_4$-$C_{12}$-alkyl) ether can preferably be controlled via one or more of the following parameters:
the temperature of the crude ester on entry into the mass transfer apparatus,
the pressure in the thermal purification of the crude ester,
the temperature of the steam-containing gas stream introduced into the mass transfer apparatus, and
the amount of the steam-containing gas stream introduced into the mass transfer apparatus.

At the same time, it is simultaneously possible to prevent the product of value, i.e. the benzenepolycarboxylic ester, from getting into the vapor in a significant amount.

The temperature in the thermal purification of the crude ester is generally in the range from 20 to 280° C., preferably in the range from 40 to 250° C., especially in the range from 100 to 220° C. This temperature corresponds to the temperature on entry of the crude ester into the mass transfer apparatus, specifically into the column. When a column having a side feed of the crude ester is used, the temperature corresponds to the temperature on entry of the crude ester via the side feed.

The thermal purification of the crude ester can be effected at ambient pressure or under reduced pressure. The thermal purification is preferably effected under reduced pressure.

More preferably, the thermal purification of the crude ester is effected at a pressure in the range from 1 to 500 mbar (absolute), especially in the range from 10 to 300 mbar (absolute).

The temperature of the steam-containing gas stream introduced into the mass transfer apparatus is preferably within a range from 100 to 200° C., more preferably 110 to 170° C.

The pressure of the steam-containing gas stream prior to entry into the mass transfer apparatus is not more than 10 bar, preferably not more than 6 bar, especially not more than 4 bar. Immediately prior to or with entry into the mass transfer apparatus, the steam-containing gas stream is expanded to the pressure of the mass transfer apparatus. This cools down the steam-containing gas stream.

Preferably, the amount of the steam-containing gas stream introduced into the mass transfer apparatus is 12 to 62 L (STP) of gas per kg of crude ester (corresponding to about 1% to 5% by weight), more preferably 25 to 50 L (STP) of gas per kg of crude ester (corresponding to about 2% to 4% by weight). (L (STP)=standard liters).

The di-($C_4$-$C_{12}$-alkyl) ether present in the vapor is at least partly discharged. This means that at least a portion of the di-($C_4$-$C_{12}$-alkyl) ether present in the vapor is not recycled into the esterification of the benzenepolycarboxylic acid with at least one $C_4$-$C_{12}$ monoalkanol or to one of the workup steps. It is thus possible, even in the case of continuous workup of the crude ester, to provide a benzenepolycarboxylic ester having a distinctly reduced content of di-($C_4$-$C_{12}$-alkyl) ether compared to known processes.

The removal of at least a portion of the di-($C_4$-$C_{12}$-alkyl) ether present in the vapor is preferably effected according to one of variants 1, 2 and 3 described hereinafter.

Variant 1:

This variant is a simple and effective process for distinctly reducing the content of di-($C_4$-$C_{12}$-alkyl) ethers in the benzenepolycarboxylic ester obtained as bottom product compared to conventional processes. As described above, it is surprisingly possible, in the thermal purification of the crude ester, to separate off at least some of the di-($C_4$-$C_{12}$-alkyl) ether present therein with the vapor. This vapor is at least partly condensed and the condensed vapor is partly or fully discharged. It is thus possible to produce a benzenepolycarboxylic ester of high purity without needing to subject existing plants for workup of crude esters by means of stripping to costly refitting.

All the aforementioned mass transfer apparatuses are suitable in principle for performance of the first process variant. Specifically, for thermal purification of the crude ester by the first variant, at least one column is used that has
a side feed for the crude ester,
a draw for the vapor in the top region of the column, and
a feed for the steam-containing gas stream in the region of the bottom of the column.

In this variant, it is possible to use a column of comparatively simple design. For instance, the column preferably does not have a rectifying section with separating internals above the feed point for the crude ester and below the draw for the vapor. However, it may be advantageous when the column has a droplet separator (demister) above the feed point for the crude ester and below the draw for the vapor. Droplet separators used may be the wire knits and wire weaves made of stainless steel, aluminum etc. that are customary for the purpose. Preferably, the column used according to this variant does not have a reflux feed above the feed point for the crude ester. Thus, in this variant, specifically no portion of the condensed vapor is recycled into the column in the top region.

In this variant, the condensed vapor comprises $C_4$-$C_{12}$-monoalkanol, di-($C_4$-$C_{12}$-alkyl) ether and up to 30% by weight of benzenepolycarboxylic ester, based on the total weight of the condensed vapor. The condensed vapor may be subjected to a distillative separation in order to at least partly isolate the benzenepolycarboxylic ester and/or $C_4$-$C_{12}$ monoalkanol present therein. It is thus possible to minimize any loss of product of value and/or raw material.

Variant 2:

In a further preferred embodiment of the process of the invention, the vapor discharged from the mass transfer apparatus is at least partly condensed, the condensate is separated into an aqueous phase and organic phase, where the organic phase comprises di-($C_4$-$C_{12}$-alkyl) ether and $C_4$-$C_{12}$ monoalkanol, a portion of the organic phase is recycled as reflux stream into the thermal purification of the crude ester, and another portion of the organic phase is discharged.

The recycling of a portion of the organic phase as reflux stream into the thermal purification of the crude ester may be continuous or discontinuous. Preferably, a portion of the organic phase is recycled continuously as reflux stream into the thermal purification of the crude ester.

The portion of the organic phase which is recycled as reflux stream into the thermal purification of the crude ester is recycled in the top region of the mass transfer apparatus above the feed point for the crude ester and, if present, the rectifying section.

For variant 2, the mass transfer apparatus used is preferably a column having a side feed for the crude ester, a rectifying section above the feed point for the crude ester and a reflux feed above the rectifying section, with recycling of a portion of the organic phase separated from the condensed vapor via the reflux feed.

It has been found that, surprisingly, the partial recycling of the organic phase in the top region of the column improves the separating effect of the column such that the benzenepolycarboxylic ester content in the vapor can be distinctly reduced. At the same time, the di-($C_4$-$C_{12}$-alkyl) ether content in the vapor is not significantly reduced, if at all. It is thus possible in this variant to prepare a di-($C_4$-$C_{12}$-alkyl) ether-depleted bottom product with a distinctly smaller loss of benzenepolycarboxylic ester.

The reflux stream into the thermal purification is preferably at a rate of 0.5 to 50 kg/h/1000 kg of crude ester, more preferably 2.5 to 25 kg/h/1000 kg of crude ester, especially 5 to 15 kg/h/1000 kg of crude ester.

In principle, it is possible that, as the reflux stream, the organic phase is replaced partly or entirely by other liquid components. For this purpose, for example, it is possible to use water, crude ester, purified benzenepolycarboxylic ester and mixtures thereof.

In a suitable execution, the constituents of the crude ester, the vapor, the organic phase, etc. are analyzed by means of gas chromatography (GC). Then the proportions of the compounds present in a sample are ascertained via their area integrals. In other words, the values are obtained directly as GC area % via the content of the individual compounds in a sample. It is possible to use normalization factors to convert the amount figures from GC area % to % by weight. A measurement series with pure compounds and mixtures of the pure compounds in different ratios has shown, for example, that the normalization factors for $C_4$-$C_{12}$ monoalkanol and benzenepolycarboxylic acid are around 1.

The condensed vapor is, as described above, subjected to a phase separation into an aqueous phase and an organic phase. The aqueous phase obtained in the separation of the condensate can be removed and discarded or used for production of steam for stripping of the crude ester.

Preferably, the organic phase separated from the condensed vapor includes 80% to 99% by weight, preferably 82% to 98.5% by weight, of at least one $C_4$-$C_{12}$ monoalkanol, based on the total weight of the organic phase.

Preferably, the organic phase separated from the condensed vapor includes not more than 9% by weight, more preferably not more than 8% by weight, especially not more than 6% by weight, of benzenepolycarboxylic ester, based on the total weight of the organic phase.

Preferably, the organic phase separated from the condensed vapor includes at least 2% by weight, preferably at least 3% by weight, of di-($C_4$-$C_{12}$-alkyl) ether, based on the total weight of the organic phase.

Preferably, the organic phase separated from the condensed vapor includes not more than 8% by weight, preferably not more than 6% by weight, of water, based on the total weight of the organic phase.

The organic phase separated from the condensed vapor may comprise further components. Preferably, each of these components is present only in a minor amount, preferably in an amount of not more than 2% by weight per component, more preferably in an amount of not more than 1% by weight per component, especially in an amount of not more than 0.5% by weight per component, based on the total weight of the organic phase. Specifically, the organic phase may comprise at least one further low-boiling component. These include, for example, $C_4$-$C_{12}$-alkenes. For instance, in the case of esterification of the benzenepolycarboxylic acid with a $C_9$ monoalkanol isomer mixture, the isomeric nonenes may be present. Further low boilers are the benzenepolycarboxylic acid used for esterification or anhydrides thereof or by-products formed therefrom. These include, for example, phthalic anhydride, phthalide, benzoic acid or benzoates. In addition, the organic phase may comprise at least one further medium-boiling component and/or at least one further high-boiling component.

More preferably, the organic phase separated from the condensed vapor comprises:
  0% to 9% by weight, preferably 0% to 6% by weight, of benzenepolycarboxylic ester,
  2% to 8% by weight, preferably 3% to 6% by weight, of at least one di-($C_4$-$C_{12}$-alkyl) ether,
  83% to 98% by weight, preferably 85% to 95% by weight, of at least one $C_4$-$C_{12}$ monoalkanols,
  0% to 8% by weight, preferably 0.1% to 6% by weight, of water,
based on the total weight of the organic phase. The organic phase separated from the condensed vapor may comprise at least one other of the aforementioned low-, medium- or high-boiling components, where the total amount thereof is preferably 0% to 5% by weight, more preferably 0% to 1% by weight, based on the total weight of the organic phase.

According to variant 2 of the process of the invention, a portion of the organic phase is discharged and a portion is recycled as reflux stream into the thermal purification of the crude ester. In a preferred embodiment, a further portion of the organic phase is recycled into the esterification of the benzenepolycarboxylic acid with the at least one $C_4$-$C_{12}$ monoalkanol. In this way, the loss of valuable reactant alcohol can be minimized and the ether content of the benzenepolycarboxylic ester can nevertheless be kept low at the same time.

The discharge of a portion of the organic phase may be discontinuous or continuous. Preferably, a portion of the organic phase is discharged discontinuously.

By definition, "closed-loop control" refers to an operation in which a parameter, the controlled variable (actual value), is continuously detected, compared with another parameter, the reference variable (target value), and influenced in the manner of assimilation to the reference variable. The closed-loop control deviation as the difference between actual value and target value is sent to the closed-loop controller, which forms a manipulated variable therefrom. The manipulated variable is the output parameter (the position) of the control element used, with the aid of which controlled intervention into the control system is effected. The control element may be part of the closed-loop controller, but in many cases is a separate device. The setting or adjustment of the control element controls the process, for example by altering a mass flow or energy flow. Examples of control elements are valves, switches, etc.

The controlled variable in the process of the invention is the content in the bottom product of di-($C_4$-$C_{12}$-alkyl) ether. The measurement can be effected by means of GC. In a suitable procedure, samples are taken and analyzed regularly. Online sampling and measurement is likewise conceivable.

In a preferred embodiment of the 2nd variant of the process of the invention, the content in the bottom product of di-($C_4$-$C_{12}$-alkyl) ether is controlled by implementing control interventions on at least one of the following manipulated variables:

the mass flow of the reflux stream of the organic phase,
the mass flow of the organic phase recycled into the esterification,
the mass flow of the organic phase discharged.

The procedure here is preferably such that a target value for the content in the bottom product of di-($C_4$-$C_{12}$-alkyl) ether and an upper and lower limit for the variance of the actual value from the target value are fixed,
the actual value of the content in the bottom product of di-($C_4$-$C_{12}$-alkyl) ether is determined,
on attainment of the upper limit for the variance of the actual value from the target value, control interventions are implemented until the content in the bottom product of di-($C_4$-$C_{12}$-alkyl) ether has fallen to the lower limit for the variance of the actual value from the target value.

The target value for the content in the bottom product of di-($C_4$-$C_{12}$-alkyl) ether is preferably not more than 1000 ppm by weight, more preferably not more than 800 ppm by weight, particularly not more than 600 ppm by weight, especially not more than 500 ppm by weight.

It has specifically been found that the content in the bottom product of di-($C_4$-$C_{12}$-alkyl) ether can advantageously be controlled by performing the discharge of a portion of the organic phase discontinuously. For this purpose, for example, the content in the bottom product of di-($C_4$-$C_{12}$-alkyl) ether can be measured at regular intervals and, on exceedance of a fixed maximum value, a portion of the organic phase can be discharged until the content in the bottom product of di-($C_4$-$C_{12}$-alkyl) ether has dropped back to a fixed minimum value. The recycling of a further portion of the organic phase into the esterification can then be effected in a manner independent from or dependent on the discontinuous discharge of a portion of the organic phase. For example, it is possible to alternately discharge a portion of the organic phase and, when there is no discharge, recycle a portion of the organic phase into the esterification.

In a further variant of the process of the invention, at least a portion of the di-($C_4$-$C_{12}$-alkyl) ether is discharged via a side draw in the column used for workup of the crude ester.

In this variant too, the mass transfer apparatus used is a column having a side feed for the crude ester, a rectifying section above the feed point for the crude ester and a reflux feed above the rectifying section, with recycling of a portion of the organic phase removed from the condensed vapor via the reflux feed.

In addition, the column has a liquid collector within the rectifying section or below the rectifying section but above the feed point for the crude ester, which collects the liquid flowing down from the top of the column and enables partial or complete discharge.

Alternatively or additionally to the discharge of a di-($C_4$-$C_{12}$-alkyl) ether-containing stream from the liquid collector, it is possible, as described above, to discharge a portion of the organic phase separated from the condensed vapor.

Variant 3:

In a further preferred embodiment of the process of the invention, the vapor discharged from the mass transfer apparatus is at least partly condensed, the condensate is separated into an aqueous phase and an organic phase, where the organic phase comprises di-($C_4$-$C_{12}$-alkyl) ether and $C_4$-$C_{12}$ monoalkanol, at least a portion of the organic phase is subjected to a separation into a di-($C_4$-$C_{12}$-alkyl) ether-enriched fraction and a $C_4$-$C_{12}$ monoalkanol-enriched fraction, and the di-($C_4$-$C_{12}$-alkyl) ether-enriched fraction is partly or fully discharged.

The further separation of at least a portion of the organic phase from the separation of the vapor condensate can reduce loss of reactant alcohol from the esterification and simultaneously further reduce the content of ether in the bottom product. It has been found that it is possible to separate the $C_4$-$C_{12}$ monoalkanol from the organic phase in high purity. With regard to the composition of the organic phase, reference is made in full to the details given for variant 2.

The high boilers present in the organic phase, specifically fractions of benzenepolycarboxylic ester removed with the vapor from the purification of the crude ester, remain here in the bottom product. The medium boilers present in the organic phase, specifically the di-($C_4$-$C_{12}$-alkyl) ether separated with the vapor in the purification of the crude ester, also remain in the bottom product and can be discharged therewith.

The distillative separation of the organic phase is effected by customary processes known to the person skilled in the art. Preference is given to using a distillation column having multiple separation stages, a top condenser, and reflux feed which enables recycling of the top product at least partly in the region of the top of the column. The distillation column may have the customary internals, such as structured packings, random packings, separating plates and column internals (e.g. distributor and collector). Rather than a stripping section, it is also possible to provide an analogous apparatus, for example an external forced circulation evaporator.

In a suitable embodiment, the organic phase is fed into the column bottoms or at the bottom end of the column beneath the internals. In that case, the column has no stripping section. It preferably has at least one theoretical plate, preferably at least 4 theoretical plates, especially at least 6 theoretical plates. Specifically, the column has 4 to 25 theoretical plates, preferably 6 to 25 theoretical plates, especially 8 to 20 theoretical plates.

In a further suitable embodiment, the organic phase is fed to the column via a side feed. The distillation column in that case has a rectifying section and a stripping section. The column in that case preferably has at least one theoretical plate in the rectifying section, preferably at least 4 theoretical plates in the rectifying section, especially at least 6 theoretical plates in the rectifying section.

The distillation is effected at ambient pressure or preferably under reduced pressure. The pressure in the distillation is preferably 0.01 bar to 1 bar, more preferably 0.02 bar to 0.5 bar, especially 0.05 bar to 0.2 bar.

The temperature in the column bottom is preferably within a range from 50 to 280° C., more preferably from 80 to 200° C.

The reflux ratio (ratio of the reflux rate to distillate removal) is preferably within a range from 0 to 10, more preferably from 0.05 to 5, especially from 0.1 to 2.

The distillative separation of at least a portion of the organic phase can be effected continuously, semicontinuously or discontinuously.

In a suitable discontinuous embodiment, the organic phase from the separation of the vapor condensate in a vessel is collected and sent therefrom to a distillative separation into a di-($C_4$-$C_{12}$-alkyl) ether-enriched fraction and a $C_4$-$C_{12}$ monoalkanol-enriched fraction. The distillative separation may be continuous or semicontinuous. In a suitable configuration for a semicontinuous separation of the organic phase, the organic phase discharged from the phase separation vessel is first guided into a collecting vessel and from that into the distillative separation. If the distillation column is capable of separating greater amounts of organic phase per unit time than discharged from the phase separation, the distillation can be conducted continuously for a certain period of time until the collecting vessel is empty. Then the distillation is stopped until enough organic phase is present again for the next distillation interval.

The $C_4$-$C_{12}$ monoalkanol-enriched fraction may be utilized as described hereinafter. The di-($C_4$-$C_{12}$-alkyl) ether-enriched fraction is discharged.

In a preferred continuous embodiment, the organic phase from the separation of the vapor condensate is sent directly to a continuous distillative separation into a di-($C_4$-$C_{12}$-alkyl) ether-enriched fraction and a $C_4$-$C_{12}$ monoalkanol-enriched fraction. The $C_4$-$C_{12}$ monoalkanol-enriched fraction may be utilized as described hereinafter. The di-($C_4$-$C_{12}$-alkyl) ether-enriched fraction is discharged.

Preferably, in variant 3 of the process of the invention as well, the mass transfer apparatus used for workup of the crude ester has a liquid reflux feed in the top region. For variant 3, the mass transfer apparatus used is especially a column having a side feed for the crude ester, a rectifying section above the feed point for the crude ester and a reflux feed above the rectifying section, with recycling of a portion of the organic phase separated from the condensed vapor via the reflux feed and/or recycling of at least a portion of the $C_4$-$C_{12}$ monoalkanol-enriched fraction obtained in the separation of the organic phase.

In a preferred embodiment, only a portion of the organic phase obtained in the separation of the condensed vapor is subjected to a separation into a di-($C_4$-$C_{12}$-alkyl) ether-enriched fraction and a $C_4$-$C_{12}$ monoalkanol-enriched fraction, and another portion of the organic phase is recycled as reflux stream into the thermal purification of the crude ester.

In a preferred embodiment, the $C_4$-$C_{12}$ monoalkanol-enriched fraction is partly or fully recycled as a reflux stream into the thermal purification of the crude ester. It is thus possible to obtain a bottom product having a very low content of di-($C_4$-$C_{12}$-alkyl) ether.

In a preferred embodiment, the $C_4$-$C_{12}$ monoalkanol-enriched fraction is partly or fully recycled into the esterification of the benzenepolycarboxylic acid with the at least one $C_4$-$C_{12}$ monoalkanol. It is thus possible to avoid a loss of valuable reactant alcohol.

The recycling of the organic phase separated from the condensed vapor and/or of the $C_4$-$C_{12}$ monoalkanol-enriched fraction obtained in the separation of the organic phase as reflux stream into the thermal purification of the crude ester may be continuous or discontinuous, preferably continuous.

Benzenepolycarboxylic Ester and Cyclohexanepolycarboxylic Ester

The above-described process enables the preparation of benzenepolycarboxylic esters with a small proportion of dialkyl ethers. They are suitable for preparation of cyclohexanedicarboxylic esters likewise having a small proportion of by-products and especially dialkyl ethers.

The benzenepolycarboxylic ester used in the process of the invention is preferably selected from compounds of the general formula (II)

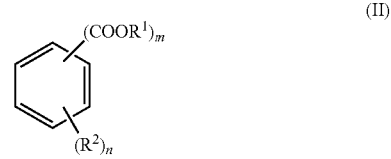

(II)

in which
m is 2, 3 or 4,
n is 0, 1, 2 or 3,
$R^1$ is independently straight-chain or branched $C_4$-$C_{12}$-alkyl, and
$R^2$ is independently straight-chain or branched $C_1$-$C_4$-alkyl.

The cyclohexanepolycarboxylic esters prepared in accordance with the invention are preferably selected from compounds of the general formula (I)

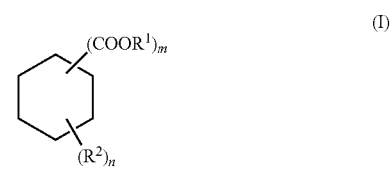

(I)

in which
m is 2, 3 or 4,
n is 0, 1, 2 or 3,
$R^1$ is independently straight-chain or branched $C_4$-$C_{12}$-alkyl, and
$R^2$ is independently straight-chain or branched $C_1$-$C_4$-alkyl.

The suitable and preferred embodiments for m, n, $R^1$ and $R^2$ specified hereinafter are equally applicable to the compounds of the formulae (I) and (II). The compounds (I) are obtained from the compounds (II) by hydrogenation of the benzene ring, such that each ring carbon atom in the compounds (I) bears one hydrogen atom more than the corresponding ring carbon atom in the compounds (II).

When m is 2 or 3, the $R^1$ radicals may be the same or different. The $C_1$-$C_4$-alkyl groups may be straight-chain or branched. When $R^1$ is an alkyl group, it is preferably methyl, ethyl, n-propyl, i-propyl, n-butyl, i-butyl, sec-butyl or tert-butyl. Preferably, m is 0, meaning that there are no $C_1$-$C_4$-alkyl substituents but exclusively hydrogen atoms, such that the ring is an aromatic benzene ring (general formula II) or a saturated cyclohexyl ring (general formula (I)).

The n $R^2$ radicals may be the same or different. The $C_4$-$C_{12}$-alkyl groups may be straight-chain or branched. $R^2$ is preferably a $C_6$-$C_{12}$-alkyl, more preferably $C_8$-$C_{10}$-alkyl. Examples of such alkyl groups are n-butyl, i-butyl, sec-butyl or tert-butyl, n-pentyl, n-hexyl, n-octyl, 2-ethylhexyl, n-nonyl, isononyl, n-decyl, isodecyl, n-undecyl, isoundecyl, n-dodecyl, isododecyl, n-tridecyl, isotridecyl, stearyl, and n-eicosyl.

The alkyl groups may each be individual isomers of the alkyl groups mentioned or mixtures of different alkyl groups. The different alkyl groups may be different isomers with the same number of carbon atoms and/or alkyl groups having a different number of carbon atoms.

The cyclohexanepolycarboxylic esters of the general formula (I) obtained in accordance with the invention are especially mono-, di-, tri- or tetraesters of the cyclohexanepolycarboxylic acids. Preferably, all carboxylic acid groups have been esterified. The esters used are alkyl esters, preferred alkyl groups $R^2$ already having been specified above.

The invention preferably affords cyclohexanepolycarboxylic esters selected from the group consisting of ring-hydrogenated mono- and dialkyl esters of phthalic acid, isophthalic acid and terephthalic acid, ring-hydrogenated mono-, di- and trialkyl esters of trimellitic acid, of trimesic acid and of hemimellitic acid, or mono-, di-, tri- and tetraalkyl esters of pyromellitic acid, where the alkyl groups $R^1$ have the definitions given above.

The benzenepolycarboxylic esters used with preference in accordance with the invention are especially selected from the group consisting of phthalic acid, isophthalic acid, terephthalic acid, trimellitic acid, trimesic acid, hemimellitic acid, pyromellitic acid and mixtures thereof. Very particular preference is given to using phthalic acid. The aforementioned acids are commercially available.

Further preferably in accordance with the invention, benzenepolycarboxylic esters of the general formula (II) are used. These are obtained, for example, by reacting at least one benzenepolycarboxylic acid selected from the group consisting of phthalic acid, isophthalic acid, terephthalic acid, trimellitic acid, trimesic acid, hemimellitic acid, pyromellitic acid and mixtures thereof with corresponding alcohols $R^1$—OH.

Alcohols used are preferably the alcohols corresponding to the $R^1$ radicals of the cyclohexanepolycarboxylic esters of the formula I.

Preference is thus given to using linear or branched alcohols having $C_4$-$C_{12}$-alkyl radicals. The alcohols used for esterification with the benzenepolycarboxylic acids may in each case be the individual isomers of the alcohols corresponding to the aforementioned R radicals or mixtures of different alcohols having isomeric alkyl radicals with the same number of carbon atoms and/or mixtures of different alcohols with a different number of carbon atoms.

The alcohols or alcohol mixtures suitable for reaction with the benzenepolycarboxylic acids may be prepared by any processes known to the person skilled in the art. Suitable processes for preparing alcohols or process steps that are employed in the preparation of alcohols are, for example:

hydroformylation with subsequent hydrogenation of the aldehydes formed, for example as disclosed in WO 92/13818;

hydrogenation of aldol products, for example as disclosed in DE-A 102 51 311;

hydration of alkenes, for example as disclosed in U.S. Pat. No. 5,136,108;

hydrogenation of carboxylic acids and carboxylic esters, especially fatty acids and fatty acid esters, for example as disclosed in U.S. Pat. No. 5,463,143;

hydrogenation of unsaturated alcohols or of carbonyl compounds, for example as disclosed in EP-A 0 394 842;

hydrogenation of epoxides, for example as disclosed in GB-A 879 803;

processes comprising a telomerization step, for example as disclosed in U.S. Pat. No. 3,091,628;

processes comprising an isomerization step, for example as disclosed in DE-A 42 28 887;

hydrolysis of sulfates, for example as disclosed in GB-A 1,165,309;

reaction of dienes with amines, for example as disclosed in DE-A 44 31 528;

enzymatic preparation of alcohols, for example as disclosed in WO 93/24644;

selective hydrogenation of dienes, for example as disclosed in U.S. Pat. No. 3,203,998;

preparation of alcohols from nitriles, for example as disclosed in EP-A 0 271 092;

preparation of alcohols by conversion of alkynes, for example as disclosed in RU 205 9597-C1; and hydrogenolysis of substituted tetrahydropyrans, for example as disclosed in GB 1,320,188.

The person skilled in the art is aware of further processes for preparing alcohols that can likewise be used for esterification of benzenepolycarboxylic acids with suitable alcohols or alcohol mixtures.

Alcohols used with preference are—as mentioned above—alcohols having $C_4$-$C_{12}$-alkyl radicals. Especially the longer-chain $C_5$-$C_{12}$ alcohols or alcohol mixtures comprising these alcohols are more preferably prepared by catalytic hydroformylation (also referred to as oxo reaction) of olefins and subsequent hydrogenation of the aldehydes formed.

Suitable hydroformylation processes are known to the person skilled in the art and are disclosed in the aforementioned documents. The alcohols and alcohol mixtures disclosed in the documents cited may be reacted with the aforementioned benzenepolycarboxylic acids to give the desired alkyl benzenepolycarboxylates or benzenepolycarboxylic ester mixtures.

$C_5$ alcohols or mixtures comprising $C_5$ alcohols, more preferably n-pentanol, may be prepared, for example, by hydroformylation of butadiene in the presence of an aqueous solution of a rhodium compound and a phosphine as catalyst. Such a process is disclosed, for example, in EP-A 0 643 031.

Suitable $C_7$ alcohol mixtures that can be used for esterification with the benzenepolycarboxylic acids are disclosed, for example, in JP-A 2000/319 444. The $C_7$ alcohol mixture is prepared by hydroformylation with subsequent hydrogenation of the aldehydes formed.

Mixtures comprising $C_8$ alcohols and preparation processes therefor are disclosed, for example, in GB-A 721 540, in which a process for preparing isooctyl alcohols proceeding from heptenes by means of hydroformylation and subsequent hydrogenation is described. A further document cited by way of example that discloses the preparation of $C_7$ alcohols or mixtures comprising these alcohols is DE-A 195 30 414.

$C_9$ alcohols or mixtures comprising $C_9$ alcohols are preferably prepared by dimerization of butenes, hydroformylation of the octenes obtained and subsequent hydrogenation of the $C_9$ aldehyde obtained.

Suitable processes and mixtures comprising $C_9$ alcohols are disclosed, for example, in WO 92/13818.

$C_{10}$ alcohols and mixtures comprising these alcohols are disclosed, for example, in WO 2003/66642.

$C_{12}$ alcohols or mixtures comprising $C_{12}$ alcohols, especially trimethylnonanol, and a process for preparation thereof are disclosed, for example, in WO 98/03462.

More preferably, according to the invention, dialkyl esters of the aforementioned cyclohexanedicarboxylic acids, especially 1,2-, 1,3- or 1,4-dialkyl esters and most preferably 1,2-dialkyl esters are obtained. It is possible here to obtain dialkyl esters or to use the corresponding dialkyl benzenedicarboxylates in which the two ester groups of the dialkyl esters bear the same alkyl radicals and ester groups in which the two ester groups of the dialkyl esters bear different alkyl groups. Examples of mixed and unmixed dialkyl esters have already been mentioned above. In addition, it is possible that the alkyl groups have the same number of carbon atoms but are straight-chain or have different branchings and hence are isomer mixtures. Such isomer mixtures may also be used when the carbon number of the alkyl groups of the dialkyl esters is different. The proportion of the different isomers of the alkyl groups generally results from the composition of the alcohols that are used for esterification of the benzenedicarboxylic acids which, after esterification, are hydrogenated in accordance with the invention to the cyclohexanedicarboxylic esters. Suitable alcohol mixtures have already been mentioned above. In the context of the present application, straight-chain or branched alkyl radicals having a particular number of carbon atoms are thus understood to mean not only the respective individual isomers but also isomer mixtures, the composition of which results—as mentioned above—from the composition of the alcohols used for esterification of the benzenedicarboxylic acids.

Straight-chain alkyl radicals in the context of the present application are understood to mean exclusively straight-chain alkyl radicals, but also mixtures of alkyl radicals that are predominantly straight-chain.

If the alkyl radicals $R^1$ of the cyclohexanepolycarboxylic esters are $C_4$-alkyl radicals, these are obtained by reaction of the benzenepolycarboxylic acids of the formula (II) with $R^1$=hydrogen with n-butanol, isobutanol, sec-butanol or tert-butanol. For preparation of benzenepolycarboxylic esters in which $R^1$ is a $C_4$, it is possible here in each case to use mixtures of the butanols mentioned or individual isomers. Preference is given to using individual isomers of butanol. The preparation of the aforementioned $C_4$ alcohols is known to the person skilled in the art.

If the alkyl radicals R of the cyclohexanepolycarboxylic esters are $C_5$- to $C_{12}$-alkyl radicals, preference is given to using $C_5$ to $C_{12}$ alcohols having degrees of branching (ISO index) of generally 0.10 to 4, preferably 0.5 to 3, more preferably 0.8 to 2 and especially 1 to 1.5, meaning that the respective alcohols are generally mixtures of different isomers.

Very particular preference is given to using $C_9$ alcohol mixtures having an ISO index of 1 to 2.5, especially nonanol mixtures having an ISO index of 1.25 or 1.6. The ISO index is a dimensionless quantity that has been determined by means of gas chromatography.

Method: Capillary GC

Apparatus: Capillary gas chromatograph with autosampler, split/splitless injection system and flame ionization detector (FID)

Chemicals: MSTFA (N-methyl-N-trimethylsilyltrifluoroacetamide) appropriate comparison substances for determination of retention times Sample preparation: 3 drops of the sample are dissolved in 1 ml of MSTFA and kept at 80° C. for 60 minutes GC conditions: Ultra-1 capillary column, length 50 m, internal diameter 0.25 mm, film thickness 0.1 micrometer, carrier gas helium Column pressure 200 psi constant Split: 80 ml/min Septum purge: 3 ml/min Oven temperature: 120° C., 25 min, isothermal Injector temperature: 250° C.

Detector temperature: 250° C. (FID)

Injection volume: 0.5 microliter

Calculation: The procedure in the calculation of the Iso index becomes apparent in the table below.

Table with Illustrative Calculation of the Iso Index:

| Component | Name | Branching | Fraction in % by vol. | Index |
|---|---|---|---|---|
| 1 | 2-Ethyl-2-methylhexanol-1 | 2 | 1.00 | 0.0200 |
| 2 | 2-Ethyl-4-methylhexanol-1 | 2 | 1.00 | 0.0200 |
| 3 | 2-Ethyl-4-methylhexanol-1 | 2 | 1.00 | 0.0200 |
| 4 | 2-Propyl-3-methylpentanol-1 | 2 | 1.00 | 0.0200 |
| 5 | 2-Propylhexanol-1 | 1 | 1.00 | 0.0100 |
| 6 | 2,5-Dimethylheptanol-1 | 2 | 1.00 | 0.0200 |
| 7 | 2,3-Dimethylheptanol-1 | 2 | 1.00 | 0.0200 |
| 8 | 2,3,4-Trimethylhexanol-1 | 3 | 1.00 | 0.0300 |
| 9 | 2-Ethylheptanol-1 | 1 | 1.00 | 0.0100 |
| 10 | 3-Ethyl-4-methylhexanol-1 | 2 | 82.00 | 1.6400 |
| 11 | 3-Ethylheptanol-1 | 1 | 1.00 | 0.0100 |
| 12 | 2-Methyloctanol-1 | 1 | 1.00 | 0.0100 |
| 13 | 4,5-Dimethylheptanol-1 | 2 | 1.00 | 0.0200 |
| 14 | 4,5-Dimethylheptanol-1 | 2 | 1.00 | 0.0200 |
| 15 | 4-Methyloctanol-1 | 1 | 1.00 | 0.0100 |
| 15a | 7-Methyloctanol-1 | 1 | 1.00 | 0.0000 |

| Component | Name | Branching | Fraction in % by vol. | Index |
|---|---|---|---|---|
| 16 | 6-Methyloctanol-1 | 1 | 1.00 | 0.0100 |
| 17 | Nonanol-1 | 0 | 1.00 | 0.0000 |
|  | Unknown component | 2 | 1.00 | 0.0200 |
|  | Total |  | 99.00 | 1.9000 |
|  |  |  | Iso index: | 1.9200 |

The $C_5$ to $C_{12}$ alcohols are prepared by the the aforementioned process. For preparation of the benzenepolycarboxylic esters in which $R^1$ is a $C_9$-alkyl radical, particular preference is given to using a nonanol mixture in which 0% to 20% by weight, preferably 0.5% to 18% by weight, more preferably 6% to 16% by weight, of the nonanol mixture has no branch, 5% to 90% by weight, preferably 10% to 80% by weight, more preferably 45% to 75% by weight, has one branch, 5% to 70% by weight, preferably 10% to 60% by weight, more preferably 15% to 35% by weight, has two branches, 0% to 10% by weight, preferably 0% to 8% by weight, more preferably 0% to 4% by weight, has three branches, and 0% to 40% by weight, preferably 0.1% to 30% by weight, more preferably 0.5% to 6.5% by weight, is other components. Other components are generally understood to mean nonanols having more than three branches, decanols or octanols, where the sum total of the components mentioned is 100% by weight.

The present invention therefore preferably relates to the process of the invention wherein the at least one derivative of the benzenepolycarboxylic acid comprises monoesters, diesters, triesters, tetraesters and anhydrides of the benzenepolycarboxylic acid. Preferably, all carboxylic acid groups have been esterified. The esters used are alkyl esters, preferred alkyl groups $R^1$ already having been specified above.

Further preferably, the present invention relates to the process of the invention wherein the at least one derivative of a benzenepolycarboxylic acid comprises mono-, di-, tri- and tetraesters of the benzenepolycarboxylic acid, wherein these have been converted by reaction with a nonanol mixture in which 0% to 20% by weight, preferably 0.5% to 18% by weight, more preferably 6% to 16% by weight, of the nonanol mixture has no branch, 5% to 90% by weight, preferably 10% to 80% by weight, more preferably 45% to 75% by weight, has one branch, 5% to 70% by weight, preferably 10% to 60% by weight, more preferably 15% to 35% by weight, has two branches, 0% to 10% by weight, preferably 0% to 8% by weight, more preferably 0% to 4% by weight, has three branches, and 0% to 40% by weight, preferably 0.1% to 30% by weight, more preferably 0.5% to 6.5% by weight, is other components, where the sum total of the components mentioned is 100% by weight.

A particularly preferred embodiment of a nonanol mixture which is used for preparation of benzenepolycarboxylic esters used with preference has the following composition:

1.73% to 3.73% by weight, preferably 1.93% to 3.53% by weight, more preferably 2.23% to 3.23% by weight, of 3-ethyl-6-methylhexanol;
0.38% to 1.38% by weight, preferably 0.48% to 1.28% by weight, more preferably 0.58% to 1.18% by weight, of 2,6-dimethylheptanol;
2.78% to 4.78% by weight, preferably 2.98% to 4.58% by weight, more preferably 3.28% to 4.28% by weight, of 3,5-dimethylheptanol;
6.30% to 16.30% by weight, preferably 7.30% to 15.30% by weight, more preferably 8.30% to 14.30% by weight, of 3,6-dimethylheptanol;
5.74% to 11.74% by weight, preferably 6.24% to 11.24% by weight, more preferably 6.74% to 10.74% by weight, of 4,6-dimethylheptanol;
1.64% to 3.64% by weight, preferably 1.84% to 3.44% by weight, more preferably 2.14% to 3.14% by weight, of 3,4,5-trimethylhexanol;
1.47% to 5.47% by weight, preferably 1.97% to 4.97% by weight, more preferably 2.47% to 4.47% by weight, of 3,4,5-trimethylhexanol, 3-methyl-4-ethylhexanol and 3-ethyl-4-methylhexanol;
4.00% to 10.00% by weight, preferably 4.50% to 9.50% by weight, more preferably 5.00% to 9.00% by weight, of 3,4-dimethylheptanol;
0.99% to 2.99% by weight, preferably 1.19% to 2.79% by weight, more preferably 1.49% to 2.49% by weight, of 4-ethyl-5-methylhexanol and 3-ethylheptanol;
2.45% to 8.45% by weight, preferably 2.95% to 7.95% by weight, more preferably 3.45% to 7.45% by weight, of 4,5-dimethylheptanol and 3-methyloctanol;
1.21% to 5.21% by weight, preferably 1.71% to 4.71% by weight, more preferably 2.21% to 4.21% by weight, of 4,5-dimethylheptanol;
1.55% to 5.55% by weight, preferably 2.05% to 5.05% by weight, more preferably 2.55% to 4.55% by weight, of 5,6-dimethylheptanol;
1.63% to 3.63% by weight, preferably 1.83% to 3.43% by weight, more preferably 2.13% to 3.13% by weight, of 4-methyloctanol;
0.98% to 2.98% by weight, preferably 1.18% to 2.78% by weight, more preferably 1.48% to 2.48% by weight of 5-methyloctanol;
0.70% to 2.70% by weight, preferably 0.90% to 2.50% by weight, more preferably 1.20% to 2.20% by weight, of 3,6,6-trimethylhexanol;
1.96% to 3.96% by weight, preferably 2.16% to 3.76% by weight, more preferably 2.46% to 3.46% by weight, of 7-methyloctanol;
1.24% to 3.24% by weight, preferably 1.44% to 3.04% by weight, more preferably 1.74% to 2.74% by weight, of 6-methyloctanol; 0.1% to 3% by weight, preferably 0.2% to 2% by weight, more preferably 0.3% to 1% by weight, of n-nonanol;
25% to 35% by weight, preferably 28% to 33% by weight, more preferably 29% to 32% by weight, of other alcohols having 9 and 10 carbon atoms;

where the sum total of the components mentioned is 100% by weight.

Such an isononanol mixture has been esterified with phthalic acid in the diisononyl phthalate of CAS No. 68515-48-0, from which the diisononyl cyclohexane-1,2-dicarboxylate with a corresponding isononyl component can be produced by the process of the invention by hydrogenating the aromatic ring. Such isononanol mixtures can be obtained via the route of zeolite-catalyzed oligomerization of $C_2$, $C_3$ and $C_4$ olefin mixtures, called the polygas process, obtaining a $C_8$ fraction from the oligomerized material and subsequently hydroformylating and hydrogenating it.

A further particularly preferred embodiment of a nonanol mixture which is used for preparation of benzenepolycarboxylic esters used with preference has the following composition:

- 6.0% to 16.0% by weight, preferably 7.0% to 15.0% by weight, more preferably 8.0% to 14.0% by weight, of n-nonanol;
- 12.8% to 28.8% by weight, preferably 14.8% to 26.8% by weight, more preferably 15.8% to 25.8% by weight, of 6-methyloctanol;
- 12.5% to 28.8% by weight, preferably 14.5% to 26.5% by weight, more preferably 15.5% to 25.5% by weight, of 4-methyloctanol;
- 3.3% to 7.3% by weight, preferably 3.8% to 6.8% by weight, more preferably 4.3% to 6.3% by weight, of 2-methyloctanol;
- 5.7% to 11.7% by weight, preferably 6.3% to 11.3% by weight, more preferably 6.7% to 10.7% by weight, of 3-ethylheptanol;
- 1.9% to 3.9% by weight, preferably 2.1% to 3.7% by weight, more preferably 2.4% to 3.4% by weight, of 2-ethylheptanol;
- 1.7% to 3.7% by weight, preferably 1.9% to 3.5% by weight, more preferably 2.2% to 3.2% by weight, of 2-propylhexanol;
- 3.2% to 9.2% by weight, preferably 3.7% to 8.7% by weight, more preferably 4.2% to 8.2% by weight, of 3,5-dimethylheptanol; 6.0% to 16.0% by weight, preferably 7.0% to 15.0% by weight, more preferably 8.0% to 14.0% by weight, of 2,5-dimethylheptanol;
- 1.8% to 3.8% by weight, preferably 2.0% to 3.6% by weight, more preferably 2.3% to 3.3% by weight, of 2,3-dimethylheptanol;
- 0.6% to 2.6% by weight, preferably 0.8% to 2.4% by weight, more preferably 1.1% to 2.1% by weight, of 3-ethyl-4-methylhexanol;
- 2.0% to 4.0% by weight, preferably 2.2% to 3.8% by weight, more preferably 2.5% to 3.5% by weight, of 2-ethyl-4-methylhexanol;
- 0.5% to 6.5% by weight, preferably 1.5% to 6% by weight, more preferably 1.5 to 5.5% by weight, of other alcohols having 9 carbon atoms;

where the sum total of the components mentioned is 100% by weight.

Such an isononanol mixture has been esterified with phthalic acid in the diisononyl phthalate of CAS No. 28553-12-0, from which the diisononyl cyclohexane-1,2-dicarboxylate with a corresponding isononyl component can be produced by the inventive hydrogenation of the aromatic ring. Such isononanol mixtures can be obtained via the route of dimerization of predominantly n-butenes to octene mixtures by means of nickel-containing catalysts, for example by the process of WO 95/14647, followed by hydroformylation of the octene mixture obtained, preferably cobalt-catalyzed hydroformylation, and hydrogenation.

Very particularly preferred products of the process of the invention are selected from the group consisting of di-n-octyl cyclohexane-1,2-dicarboxylate, diisooctyl cyclohexane-1,2-dicarboxylate, di-(2-ethylhexyl) cyclohexane-1,2-dicarboxylate, di-n-nonyl cyclohexane-1,2-dicarboxylate, diisononyl cyclohexane-1,2-dicarboxylate, di-(2-propylheptyl) cyclohexane-1,2-dicarboxylate, di-n-decyl cyclohexane-1,2-dicarboxylate, diisodecyl cyclohexane-1,2-dicarboxylate and mixtures thereof.

Further products obtained with preference in accordance with the invention are the cyclohexane-1,2-dicarboxylic esters that are disclosed in WO 99/32427 and listed once again below:

- di(isononyl) cyclohexane-1,2-dicarboxylates, obtainable by the inventive hydrogenation of a di(isononyl) phthalate having CAS No. 68515-48-0;
- di(isononyl) cyclohexane-1,2-dicarboxylates, obtainable by the inventive hydrogenation of a di(isononyl) phthalate having CAS No. 28553-12-0, based on n-butene;
- di(isononyl) cyclohexane-1,2-dicarboxylates, obtainable by the inventive hydrogenation of a di(isononyl) phthalate having CAS No. 28553-12-0, based on isobutene;
- a 1,2-di-$C_9$ ester of cyclohexanedicarboxylic acid, obtainable by the inventive hydrogenation of a di(nonyl) phthalate having CAS No. 68515-46-8;
- a di(isodecyl) cyclohexane-1,2-dicarboxylate obtainable by the inventive hydrogenation of a di(isodecyl) phthalate having CAS No. 68515-49-1;
- a di(isodecyl) cyclohexane-1,2-dicarboxylate obtainable by the inventive hydrogenation of a di(isodecyl) phthalate, consisting mainly of di-(2-propylheptyl) phthalate.

In addition, the commercially available benzenecarboxylic esters having the trade names Jayflex DINP (CAS No. 68515-25 48-0), Jayflex DIDP (CAS No. 68515-49-1), Palatinol 9-P, Vestinol 9 (CAS No. 28553-12-0), Palatinol N (CAS No. 28553-12-0), Jayflex DIOP (CAS No. 27554-26-3), Palatinol AH (CAS No. 117-81-7) and Palatinol Z (CAS No. 26761-40-0) are also suitable reactants for the process of the invention.

Process for Preparing a Cyclohexanepolycarboxylic Ester

The benzenepolycarboxylic esters from the above-described workup of a crude ester, owing to their low content of by-products, especially of di-($C_4$-$C_{12}$-alkyl) ethers, are advantageously suitable for preparation of cyclohexanepolycarboxylic esters.

The invention further provides a process for preparing a cyclohexanepolycarboxylic ester, in which i) a crude ester from the esterification of a benzenepolycarboxylic acid with at least one $C_4$-$C_{12}$ monoalkanol is provided, ii) the crude ester provided in step i) is subjected to a workup as defined above to obtain a benzenepolycarboxylic ester depleted of di-($C_4$-$C_{12}$-alkyl) ethers compared to the crude ester, iii) the benzenepolycarboxylic ester depleted of di-($C_4$-$C_{12}$-alkyl) ethers which is obtained in step ii) is subjected to a hydrogenation with a hydrogen-containing gas in the presence of a hydrogenation catalyst.

With regard to the provision of the crude ester from the esterification of a benzenepolycarboxylic acid with at least one $C_4$-$C_{12}$ monoalkanol in step i), reference is made to the remarks above in full. In addition, with regard to the workup of the crude ester in step ii), reference is made to the above remarks in full.

It has been found that cyclohexanepolycarboxylic esters are obtained with a reduced proportion of by-products, especially di-($C_4$-$C_{12}$-alkyl) ethers, when the hydrogenation of the corresponding benzenepolycarboxylic esters is effected by the preparation process described hereinafter. More particularly, it is thus possible to prepare with a small proportion of diisononyl ethers.

The inventive contacting of the at least one benzenepolycarboxylic ester with a hydrogen-comprising gas results in a hydrogenation of these compounds in order to obtain the desired at least one cyclohexanepolycarboxylic ester. Preferably in accordance with the invention, only the aromatic system is hydrogenated, i.e. reduced, in order to obtain the corresponding saturated cycloaliphatic system, meaning that any further reducible groups present in the at least one substrate are preferably not reduced in accordance with the invention.

Catalysts suitable for the process of the invention comprise at least one active metal that can be used as an all-active catalyst or applied to a support.

Active metals used may in principle be all metals of transition group VIII of the Periodic Table. Active metals used are preferably platinum, rhodium, palladium, cobalt, nickel or ruthenium, or a mixture of two or more thereof, with use of ruthenium or nickel in particular as active metal. Among the likewise usable metals of transition group I, II or VII of the Periodic Table, all of which are likewise usable in principle, preference is given to using copper, zinc and/or rhenium.

Corresponding catalysts are described, for example, in *Ullmann's Encyclopedia of Industrial Chemistry* Vol. 18, *Hydrogenation and Dehydrogenation* chapter, pages 483-541.

Suitable active metals may have been applied to an inert support; suitable support materials are, for example, activated carbons, metal oxides and zeolites. Preference is given to catalysts comprising, as support material, aluminum oxide, silicon dioxide, charcoal or mixed oxides comprising aluminum oxide and/or silicon dioxide. Suitable materials are described, for example, in *Ullmann's Encyclopedia of Industrial Chemistry* Vol. 17, *Heterogeneous Catalysis and Solid Catalysts*, 2. *Development and Types of Solid Catalysts* chapter, pages 483-541.

The content of the active metal in the case of platinum metals (ruthenium, rhodium, palladium, platinum) is generally 0.01% to 30% by weight, preferably 0.01% to 5% by weight and especially 0.1% to 5% by weight, based in each case on the total weight of the catalyst used, and the contents used with preference in catalysts 1 to 3 used with preference that are described hereinafter are stated individually once again in the discussion of these catalysts. In the case of nickel or cobalt as active metal, the active metal content is generally between 5% and 100% by weight, based on the total weight of the catalyst.

There follows a detailed description of the catalysts used with preference in accordance with the invention. The description is made by way of example with reference to the use of ruthenium as active metal. The details below are also applicable to the other suitable active metals as defined above.

Catalyst 1

The catalysts 1 used in accordance with the invention may be prepared industrially by applying at least one metal of transition group VIII of the Periodic Table and optionally at least one metal of transition group I or VII of the Periodic Table to a suitable support.

The application can be achieved by impregnating the support in aqueous metal salt solutions, for example aqueous ruthenium salt solutions, by spray application of appropriate metal salt solutions to the support, or by other suitable methods. Suitable metal salts of transition group I, VII or VIII of the Periodic Table are the nitrates, nitrosylnitrates, halides, carbonates, carboxylates, acetylacetonates, chloro complexes, nitrito complexes or ammine complexes of the corresponding metals, preference being given to the nitrates and nitrosylnitrates.

In catalysts comprising not only the metal of transition group VIII of the Periodic Table but also further metals applied to the support as active metal, the metal salts or metal salt solutions may be applied simultaneously or successively.

The supports coated or impregnated with the metal salt solution are subsequently dried, preferably at temperatures of 100 to 150° C., and optionally calcined at temperatures of 200 to 600° C., preferably of 350 to 450° C. In the case of separate impregnation, the catalyst is dried after each impregnation step and optionally calcined as described above. The sequence in which the active components are applied by impregnation can be chosen freely here.

Subsequently, the coated and dried and optionally calcined supports are activated by treatment in a gas stream comprising free hydrogen at temperatures of 30 to 600° C., preferably of 150 to 450° C. The gas stream preferably consists of 50% to 100% by volume of $H_2$ and 0% to 50% by volume of $N_2$.

The metal salt solution(s) is/are applied to the support(s) in such an amount that the total content of active metal, based in each case on the total weight of the catalyst, is 0.01% to 30% by weight, preferably 0.01% to 5% by weight, further preferably 0.01% to 1% by weight, and especially 0.05% to 1% by weight.

The metal surface area on the catalyst 1 preferably totals 0.01 to 10 $m^2/g$, further preferably 0.05 to 5 $m^2/g$ and especially 0.05 to 3 $m^2/g$ of the catalyst. The metal surface area is determined by means of the chemisorption method described by J. Lemaitre et al. in *Characterization of Heterogeneous Catalysts*, ed. Francis Delanney, Marcel Dekker, New York 1984, p. 310-324.

In catalyst 1 used in accordance with the invention, the ratio of the surface areas of the active metal(s) and the catalyst support is preferably less than 0.05, the lower limit being 0.0005.

The support materials usable for preparation of the catalysts used in accordance with the invention are those that are macroporous and have an average pore diameter of at least 50 nm, preferably at least 100 nm, especially at least 500 nm, and have a BET surface area of not more than 30 $m^2/g$, preferably not more than 15 $m^2/g$, further preferably not more than 10 $m^2/g$, especially not more than 5 $m^2/g$ and further preferably not more than 3 $m^2/g$. The average pore diameter of the support is preferably 100 nm to 200 μm, further preferably 500 nm to 50 μm. The surface area of the support is preferably 0.2 to 15 $m^2/g$, further preferably 0.5 to 10 $m^2/g$, especially 0.5 to 5 $m^2/g$ and further preferably 0.5 to 3 $m^2/g$.

The surface area of the support is determined by the BET method by $N_2$ adsorption, especially to DIN 66131. The average pore diameter and the pore size distribution are determined by Hg porosimetry, especially to DIN 66133.

The pore size distribution of the support may preferably be virtually bimodal, and the pore diameter distribution with maxima at about 600 nm and about 20 μm in the bimodal distribution constitutes a specific embodiment of the invention.

Preference is further given to a support having a surface area of 1.70 to 180 $m^2/g$, for example 1.75 $m^2/g$, having this bimodal distribution of pore diameter. The pore volume of this preferred support is preferably about 0.50 to 0.60 ml/g, for example 0.53 ml/g.

Examples of usable macroporous support materials are the following materials having macropores: activated carbon, silicon dioxide, aluminum oxide, silicon carbide, titanium dioxide, zirconium dioxide, magnesium oxide, zinc oxide or mixtures of two or more thereof; preference is given to using aluminum oxide and zirconium dioxide.

Further details with regard to catalyst 1 and its preparation can be found in DE-A 25 196 24 484, the content of which in this regard is incorporated fully into the present application by reference.

Catalyst 2

The catalysts 2 used in accordance with the invention comprise one or more metals of transition group VIII of the Periodic Table as active component(s) on a support, as defined herein. Preference is given to using ruthenium, palladium and/or rhodium as active component(s).

The catalysts 2 used in accordance with the invention may be prepared industrially by applying at least one active metal of transition group VIII of the Periodic Table, preferably ruthenium or palladium, and optionally at least one metal of transition group I or VII of the Periodic Table to a suitable support. The application can be achieved by impregnating the support in aqueous metal salt solutions, for example ruthenium or palladium salt solutions, by spray application of appropriate metal salt solutions to the support, or by other suitable methods. Suitable metal salts for preparation of the metal salt solutions are the nitrates, nitrosylnitrates, halides, carbonates, carboxylates, acetylacetonates, chloro complexes, nitrito complexes or ammine complexes of the corresponding metals, preference being given to the nitrates and nitrosylnitrates.

In the case of catalysts comprising two or more active metals applied to the support, the metal salts or metal salt solutions may be applied simultaneously or successively.

The supports coated or impregnated with the metal salt solution are subsequently dried, preference being given to temperatures of 100 to 150° C. These supports can optionally be calcined at temperatures of 200 to 600° C., preferably of 350 to 450° C. Subsequently, the coated supports are activated by treatment in a gas stream comprising free hydrogen at temperatures of 30 to 600° C., preferably of 100 to 450° C. and especially of 100 to 300° C. The gas stream consists preferably of 50% to 100% by volume of $H_2$ and 0% to 50% by volume of $N_2$.

If multiple active metals are applied to the supports and the application is effected successively, the support can be dried after each application or impregnation at temperatures of 100 to 150° C. and optionally calcined at temperatures of 200 to 600° C. The sequence in which the metal salt solution is applied, or applied by impregnation, may be chosen here arbitrarily.

The metal salt solution is applied to the support(s) in such an amount that the content of active metal is 0.01% to 30% by weight, preferably 0.01% to 10% by weight, further preferably 0.01% to 5% by weight and especially 0.3% to 1% by weight, based on the total weight of the catalyst.

The metal surface area on the catalyst preferably totals 0.01 to 10 $m^2/g$, more preferably 0.05 to 5 $m^2/g$ and further preferably 0.05 to 3 $m^2/g$ of the catalyst. The metal surface area was measured by means of the chemisorption method as described by J. Lemaitre et al. in *Characterization of Heterogeneous Catalysts*, ed. Francis Delanney, Marcel Dekker, New York (1984) p. 310-324.

In catalyst 2 used in accordance with the invention, the ratio of the surface areas of the at least one active metal and the catalyst support is less than 0.3, preferably less than 0.1 and especially 0.05 or less, the lower limit being 0.0005.

The support materials usable for preparation of the catalysts 2 used in accordance with the invention have macropores and mesopores.

The supports usable with preference in accordance with the invention have a pore distribution wherein 5% to 50%, preferably 10% to 40%, further preferably 10% to 30% and especially 15% to 25% of the pore volume is formed by macropores having pore diameters in the range from 50 nm to 10 000 nm, and 50% to 95%, preferably 55% to 90%, further preferably 70% to 90% and especially 75% to 85% of the pore volume by mesopores having a pore diameter of 2 to 50 nm, wherein the sum totals of the proportions of the pore volumes each add up to 100%.

The total pore volume of the supports used in accordance with the invention is 0.05 to 1.5 $cm^3/g$, preferably 0.1 to 1.2 $cm^3/g$ and especially 0.3 to 1.0 $cm^3/g$. The average pore diameter of the supports used in accordance with the invention is 5 to 20 nm, preferably 8 to 15 nm and especially 9 to 12 nm.

The surface area of the support is preferably 50 to 500 $m^2/g$, further preferably 200 to 350 $m^2/g$ and especially 250 to 300 $m^2/g$ of the support.

The surface area of the support is determined by the BET method by $N_2$ adsorption, especially to DIN 66131. The average pore diameter and the size distribution are determined by Hg porosimetry, especially to DIN 66133.

Although it is possible in principle to use all support materials known in catalyst production, i.e. having the above-defined pore size distribution, preference is given to using the following materials having macropores: activated carbon, silicon carbide, aluminum oxide, silicon dioxide, titanium dioxide, zirconium dioxide, magnesium oxide, zinc oxide or mixtures thereof; further preferably aluminum oxide and zirconium dioxide.

A specific embodiment is catalysts comprising, as active metal, ruthenium alone or in combination with at least one further metal of transition group I, VII or VIII of the Periodic Table of the Elements, in an amount of the active metal of 0.01% to 30% by weight, based on the total weight of the catalyst, applied to a support, or catalysts comprising, as active metal, palladium alone or in combination with at least one further metal of transition group I, VII or VIII of the Periodic Table of the Elements, in an amount of the active metal of 0.01% to 30% by weight, based on the total weight of the catalyst, applied to a support, where 5% to 50% of the pore volume of the support in each case is formed by macropores having a pore diameter in the range from 50 nm to 10 000 nm and 50% to 95% of the pore volume of the support by mesopores having a pore diameter in the range from 2 to less than 50 nm, where the sum total of the pore volumes adds up to 100%. More particularly, the active metal used is ruthenium alone or in combination with at least one further metal of transition group I, VII or VIII of the Periodic Table of the Elements.

Further details with regard to catalyst 2 and its preparation can be found in EP-A-0814098 and DE-A 196 24 485, as one of the priority documents of EP-A-0814098. The content of these documents is incorporated fully into the present application by reference.

The use of catalysts 2 as hydrogenation catalysts is a particularly preferred embodiment of the process of the invention.

Catalyst 3

The catalysts 3 used in accordance with the invention may be prepared industrially by applying an active metal of transition group VIII of the Periodic Table and optionally at least one metal of transition group I or VII of the Periodic Table to a suitable support. The application can be achieved by impregnating the support in aqueous metal salt solutions, for example ruthenium salt solutions, by spray application of appropriate metal salt solutions to the support, or by other suitable methods. Suitable ruthenium salts for preparation of the ruthenium salt solutions, and also suitable metal salts of transition group I, VII or VIII, are the nitrates, nitrosylnitrates, halides, carbonates, carboxylates, acetylacetonates, chloro complexes, nitrito complexes or ammine complexes of the corresponding metals; preference is given to the nitrates and nitrosylnitrates.

In the case of catalysts comprising two or more metals applied to the support, the metal salts or metal salt solutions may be applied simultaneously or successively.

The supports coated or impregnated with the ruthenium salt or metal salt solution are then dried, preferably at temperatures of 100 to 150° C., and optionally calcined at temperatures of 200 to 600° C.

Subsequently, the coated supports are activated by treatment of the coated supports in a gas stream comprising free hydrogen at temperatures of 30 to 600° C., preferably of 150 to 450° C. The gas stream consists preferably of 50% to 100% by volume of $H_2$ and 0% to 50% by volume of $N_2$.

If not only the active metal of transition group VIII of the Periodic Table but also metals of transition group I or VII are applied to the supports and the application is effected successively, the support can be dried after each application or impregnation at temperatures of 100 to 150° C. and optionally calcined at temperatures of 200 to 600° C. The sequence in which the metal salt solutions are applied, or applied by impregnation, may be chosen here arbitrarily.

The metal salt solution is applied to the support(s) in such an amount that 0.01% to 30% by weight, based on the total weight of the catalyst, of active metal has been applied to the support. This amount is preferably 0.2% to 15% by weight, more preferably about 0.5% by weight.

The metal surface area on the catalyst 3 preferably totals 0.01 to 10 $m^2/g$, more preferably 0.05 to 5 $m^2/g$, especially 0.05 to 3 $m^2$ per g of the catalyst.

The support materials usable for preparation of the catalysts 3 used in accordance with the invention are preferably those that are macroporous and have an average pore diameter of at least 0.1 µm, preferably at least 0.5 µm, and a surface area of not more than 15 $m^2/g$, preferably not more than 10 $m^2/g$, more preferably not more than 5 $m^2/g$, especially not more than 3 $m^2/g$.

The average pore diameter of the support is preferably within a range from 0.1 to 200 µm, especially from 0.5 to 50 µm. The surface area of the support is preferably 0.2 to 15 $m^2/g$, more preferably 0.5 to 10 $m^2/g$, particularly 0.5 to 5 $m^2/g$, especially 0.5 to 3 $m^2/g$, of the support.

The surface area of the support is determined by the BET method by $N_2$ adsorption, especially to DIN 66131. The average pore diameter and the pore size distribution were determined by Hg porosimetry, especially to DIN 66133. The pore size distribution of the support may preferably be virtually bimodal, and the pore diameter distribution with maxima at about 0.6 µm and about 20 µm in the bimodal distribution constitutes a specific embodiment of the invention.

Particular preference is given to a support having a surface area of about 1.75 $m^2/g$, having this bimodal distribution of pore diameter. The pore volume of this preferred support is preferably about 0.53 ml/g.

Usable macroporous support materials are, for example, the following materials having macropores activated carbon, silicon carbide, aluminum oxide, silicon dioxide, titanium dioxide, zirconium dioxide, magnesium oxide, zinc oxide or mixtures thereof. Preference is given to aluminum oxide and zirconium dioxide.

Further details with regard to catalyst 3 and its preparation can be found in DE 196 04 791.9, the content of which in this regard is incorporated fully into the present application by reference.

Catalyst 4:

Particularly suitable in accordance with the invention are eggshell catalysts (catalysts 4) comprising an active metal on a support. Corresponding eggshell catalysts are specified in WO 2011/082991. The content of WO 2011/082991 is incorporated fully into the present application by reference.

Particular preference is given to a corresponding eggshell catalyst comprising an active metal selected from the group consisting of ruthenium, rhodium, palladium, platinum and mixtures thereof, applied to a support material comprising silicon dioxide, where the pore volume of the support material is 0.6 to 1.0 ml/g, determined by Hg porosimetry, the BET surface area is 280 to 500 $m^2/g$, and at least 90% of the pores present have a diameter of 6 to 12 nm.

The present invention therefore preferably relates to the process of the invention, wherein the catalyst used is an eggshell catalyst comprising an active metal selected from the group consisting of ruthenium, rhodium, palladium, platinum and mixtures thereof, applied to a support material comprising silicon dioxide, where the pore volume of the support material is 0.6 to 1.0 ml/g, determined by Hg porosimetry, the BET surface area is 280 to 500 $m^2/g$, and at least 90% of the pores present have a diameter of 6 to 12 nm.

The eggshell catalyst used with preference comprises an active metal selected from the group consisting of ruthenium, rhodium, palladium, platinum and mixtures thereof, preferably ruthenium, most preferably ruthenium as the sole active metal.

In the eggshell catalyst used with preference in accordance with the invention, the amount of the active metal is generally less than 1% by weight, preferably 0.1% to 0.5% by weight, more preferably 0.25 to 0.35% by weight, based on the total weight of the catalyst.

Eggshell catalysts are known per se to those skilled in the art. In the context of the present invention, the term "eggshell catalyst" means that the at least one active metal present, preferably ruthenium, is present predominantly in an outer shell of the support material.

In the eggshell catalysts used with preference in accordance with the invention, preferably 40% to 70% by weight, more preferably 50% to 60% by weight, of the active metal, based on the total amount of the active metal, is present in the shell of the catalyst up to a penetration depth of 200 µm. In a particularly preferred embodiment, 60% to 90% by weight, most preferably 70% to 80% by weight, of the active metal, based on the total amount of the active metal, is present in the shell of the catalyst up to a penetration depth of 500 µm. The aforementioned data are ascertained by means of SEM (scanning electron microscopy) EPMA (electron probe microanalysis)-EDXS (energy dispersive X-ray spectroscopy) and are average values. Further information relating to the abovementioned analysis methods and techniques are disclosed, for example, in *Spectroscopy in Catalysis* by J. W. Niemantsverdriet, VCH, 1995 or *Handbook of Microscopy* by S. Amelinckx et al. In order to ascertain the penetration depth of the active metal particles, several catalyst particles (for example 3, 4 or 6) are superficially ground. By means of line scans, the profiles of the active metal/Si concentration ratios are then detected. On each measurement line, multiple measurement points, for example 15 to 20, are measured at equal intervals; the measurement spot size is about 10 µm*10 µm. After integration of the amount of active metal over the depth, it is possible to determine the frequency of the active metal in a zone.

Most preferably, the amount of the active metal, based on the concentration ratio of active metal to Si, at the surface of the eggshell catalyst is 2% to 25%, preferably 4% to 10%, more preferably 4% to 6%, determined by means of SEM EPMA-EDXS. The surface is analyzed by means of area analyses of areas of 800 μm*2000 μm and with an information depth of about 2 μm. The element composition is determined in % by weight (normalized to 100% by weight). The average concentration ratio (active metal/Si) is averaged over 10 measurement areas.

In the context of the present invention, the surface of the eggshell catalyst is understood to mean the outer shell of the catalyst up to a penetration depth of about 2 μm. This penetration depth corresponds to the information depth in the aforementioned surface analysis.

Very particular preference is given to an eggshell catalyst in which the amount of the active metal, based on the weight ratio of active metal to Si (w/w in %), is 4% to 6% at the surface of the eggshell catalyst, 1.5% to 3% at a penetration depth of 50 μm, and 0.5% to 2% in the penetration depth range from 50 μm to 150 μm, determined by means of SEM EPMA (EDXS). The values cited are average values.

In addition, the size of the active metal particles preferably decreases with increasing penetration depth, determined by means of (FEG)-TEM analysis.

The active metal in the eggshell catalyst of the invention is preferably in partly or fully crystalline form. In preferred cases, ultrafinely crystalline active metal can be detected by means of SAD (Selected Area Diffraction) in the shell of the eggshell catalyst of the invention.

The eggshell catalysts preferred in accordance with the invention may additionally comprise alkaline earth metal ions ($M^{2+}$), i.e. M=Be, Mg, Ca, Sr and/or Ba, especially Mg and/or Ca, very particularly Mg. The content of alkaline earth metal ion(s) ($M^{2+}$) in the catalyst is preferably 0.01% to 1% by weight, especially 0.05% to 0.5% by weight, very particularly 0.1% to 0.25% by weight, based in each case on the weight of the silicon dioxide support material.

An essential constituent of the catalyst preferred in accordance with the invention is the support material comprising silicon dioxide, preferably amorphous silicon dioxide. What is meant by the term "amorphous" in this connection is that the proportion of crystalline silicon dioxide phases accounts for less than 10% by weight of the support material. The support materials used for preparation of the catalysts may, however, have superstructures that are formed by regular arrangement of pores in the support material.

Useful support materials in principle include amorphous silicon dioxide types consisting at least to an extent of 90% by weight of silicon dioxide, where the remaining 10% by weight, preferably not more than 5% by weight, of the support material may also be another oxidic material, e.g. MgO, CaO, $TiO_2$, $ZrO_2$ and/or $Al_2O_3$.

In a preferred embodiment of the invention, the support material is halogen-free, especially chlorine-free, meaning that the halogen content in the support material is generally less than 500 ppm by weight, for example in the range from 0 to 400 ppm by weight. Preference is thus given to an eggshell catalyst comprising less than 0.05% by weight of halide (determined by ion chromatography), based on the total weight of the catalyst. More preferably, the halide content of the support material is below the analytical detection limit. Preference is given to support materials comprising silicon dioxide that have a specific surface area in the range from 280 to 500 m²/g, more preferably 280 to 400 m²/g, most preferably 300 to 350 m²/g (BET surface area to DIN 66131). They may be of natural origin or have been synthetically produced. Examples of suitable amorphous support materials based on silicon dioxide are silica gels, kieselguhr, fumed silicas and precipitated silicas. In a preferred embodiment of the invention, the catalysts have silica gels as support materials.

According to the invention, the pore volume of the support material is 0.6 to 1.0 ml/g, preferably 0.65 to 0.9 ml/g, for example 0.7 to 0.8 ml/g, determined by Hg porosimetry (DIN 66133). In the eggshell catalyst preferred in accordance with the invention, at least 90% of the pores present have a pore diameter of 6 to 12 nm, preferably 7 to 11 nm, more preferably 8 to 10 nm. The pore diameter can be determined by methods known to the person skilled in the art, for example by Hg porosimetry or $N_2$ physisorption. In a preferred embodiment, at least 95%, more preferably at least 98%, of the pores present have a pore diameter of 6 to 12 nm, preferably 7 to 11 nm, more preferably 8 to 10 nm.

In the eggshell catalyst preferred in accordance with the invention, in a preferred embodiment, there are no pores smaller than 5 nm. In addition, in the eggshell catalyst preferred in accordance with the invention, there are no pores larger than 25 nm, especially larger than 15 nm. In this connection, "no pores" means that no pores having these diameters are found by standard test methods, for example Hg porosimetry or $N_2$ physisorption. In the eggshell catalyst preferred in accordance with the invention, within the scope of measurement accuracy of the analysis used, there are no macropores, but exclusively mesopores.

In the eggshell catalyst preferred in accordance with the invention, particular preference is given to using shaped bodies of the support material that are obtainable, for example, by extrusion, strand pressing or tableting and may have the shape, for example, of spheres, tablets, cylinders, extrudates, rings or hollow cylinders, stars and the like, more preferably spheres. The dimensions of these shaped bodies typically vary within the range from 0.5 mm to 25 mm. Preference is given to using catalyst spheres having sphere diameters of 1.0 to 6.0 mm, more preferably 2.5 to 5.5 mm. In the eggshell catalyst preferred in accordance with the invention, the dispersity of the active metal is preferably 30% to 60%, more preferably 30% to 50%. Methods of measuring the dispersity of the active metal are known per se to the person skilled in the art, for example through pulse chemisorption, wherein the determination of the precious metal dispersion (specific metal surface area, crystallite size) is conducted by a CO pulse method (DIN 66136(1-3).

In the eggshell catalyst preferred in accordance with the invention, the surface area of the active metal is preferably 0.2 to 0.8 m²/g, more preferably 0.3 to 0.7 m²/g. Methods of measuring the surface area of the active metal are known per se to the person skilled in the art.

The eggshell catalysts preferred in accordance with the invention are prepared, for example, by first soaking the support material with a solution comprising a precursor compound of the active metal once or more than once, and drying and then reducing the resultant solids. The individual process steps are known per se to the person skilled in the art and are described in WO 2011/082991.

The use of catalysts 4 as hydrogenation catalysts is a further particularly preferred embodiment of the process of the invention.

Catalyst 5:

Likewise suitable in accordance with the invention are catalysts 5 having an active metal on a mesoporous support according to WO 2004/046078. Catalyst 5 comprises one or more catalytically active metal(s), such as platinum, palladium, ruthenium or mixtures thereof, deposited on a catalyst support material comprising one or more ordered mesoporous materials. The content of WO 2004/046078 is incorporated fully into the present application by reference.

Catalyst 6:

Likewise suitable in accordance with the invention are catalysts 6 having an active metal on a mesoporous support according to U.S. Pat. No. 7,893,295. The catalyst specified therein comprises one or more catalytically active metal(s), such as platinum, palladium, ruthenium or mixtures thereof, deposited on a catalyst support material comprising one or more ordered mesoporous materials. The content of U.S. Pat. No. 7,893,295 is incorporated fully into the present application by reference.

Catalyst 7:

Likewise suitable in accordance with the invention are mesoporous metal/support catalysts 7 according to DE 10225565. This catalyst comprises at least one group 8 metal on or in a support material having an average pore diameter of 25 to 50 nm and a specific surface area of more than 30 $m^2/g$. The content of DE 10225565 is incorporated fully into the present application by reference.

Catalyst 8:

Likewise suitable in accordance with the invention are catalysts 8 based on nickel/zinc according to DE 10146847. The content of DE 10146847 is incorporated fully into the present application by reference.

Catalyst 9:

Likewise suitable in accordance with the invention are microporous metal catalysts 9 on titanium dioxide supports according to WO 04/009526. The content of WO 04/009526 is incorporated fully into the present application by reference.

The temperature in the hydrogenation is preferably within a range from 50 to 250° C., more preferably from 70 to 200° C., especially from 90 to 150° C.

The absolute pressure in the hydrogenation is preferably within a range from 50 to 330 bar, more preferably within a range from 200 to 300 bar, especially within a range from 220 to 270 bar.

The process of the invention can be performed either continuously or discontinuously, preference being given to continuous performance of the process.

The benzenepolycarboxylic esters are preferably hydrogenated over a fixed bed catalyst in trickle mode or in liquid phase mode. In trickle mode, the liquid reaction medium in the reactor is allowed to trickle over the catalyst bed disposed in the reactor, with formation of a thin liquid film on the catalyst. When working in liquid phase mode, a hydrogen-containing gas is introduced into the reactor flooded with the liquid reaction medium, with the hydrogen passing through the catalyst bed in ascending gas bubbles.

The hydrogen-comprising gas can be guided over the catalyst either in cocurrent with the solution of the reactant to be hydrogenated or in countercurrent. The hydrogenation can also be performed discontinuously in batchwise mode.

In the continuous process regime, catalyst hourly space velocity is preferably 0.05 to 120 kg (benzenepolycarboxylic acid)/(L(catalyst)×h), more preferably 0.5 to 12 kg (benzenepolycarboxylic acid)/(L(catalyst)×h).

The process of the invention can be performed in the absence or presence of a solvent or diluent, meaning that it is unnecessary to perform the process in solution.

However, preference is given to using a solvent or diluent. The solvent or diluent used may be any suitable solvent or diluent. The selection here is not critical, provided that the solvent or diluent used is capable of forming a homogeneous solution with the at least one benzenepolycarboxylic ester.

For example, the solvents or diluents may also comprise water. For example, a solvent or diluent is selected from the group consisting of straight-chain or cyclic ethers, for example tetrahydrofuran or dioxane, aliphatic alcohols in which the alkyl radical has preferably 1 to 10 carbon atoms, especially 3 to 6 carbon atoms, for example i-propanal, n-butanol, i-butanol, n-hexanol and mixtures thereof.

The amount of the solvent or diluent used is not particularly restricted and can be selected freely as required, although preference is given to those amounts that lead to a 10% to 70% by weight solution of the at least one benzenepolycarboxylic ester intended for hydrogenation.

More preferably, in the context of the process of the invention, the product formed in the hydrogenation, i.e. the corresponding cyclohexanepolycarboxylic ester, is used as solvent, optionally alongside other solvents or diluents. In each case, a portion of the product formed in the process may be mixed into the benzenepolycarboxylic ester yet to be hydrogenated. Based on the weight of the compound intended for hydrogenation, preference is given to mixing in 1 to 30 times, preferably 5 to 20 times, especially 5 to 10 times, the amount of the reaction product as solvent or diluent.

The process of the invention is generally performed at a superficial velocity of 1 to 500 m/h; the process of the invention is preferably performed at a superficial velocity of 5 to 300 m/h; the process of the invention is more preferably performed at a superficial velocity of 10 to 180 m/h.

The invention further provides a composition comprising at least one benzenepolycarboxylic ester of the general formula (II)

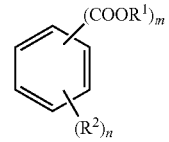

(II)

in which
  m is 2, 3 or 4,
  n is 0, 1, 2 or 3,
  $R^1$ is independently straight-chain or branched $C_4$-$C_{12}$-alkyl, and
  $R^2$ is independently straight-chain or branched $C_1$-$C_4$-alkyl,
and 1 to 500 ppm by weight, based on the total weight of the composition, of at least one ether of the general formula $R^1$—O—$R^1$.

The invention further provides a composition comprising diisononyl phthalate and 10 to 500 ppm by weight, based on the total weight of the composition, of diisononyl ether.

The invention further provides a composition comprising at least one cyclohexanepolycarboxylic ester of the general formula (I)

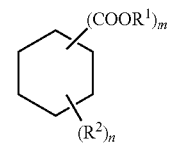

(I)

in which
- m is 2, 3 or 4,
- n is 0, 1, 2 or 3,
- $R^1$ is independently straight-chain or branched $C_4$-$C_{12}$-alkyl, and
- $R^2$ is independently straight-chain or branched $C_1$-$C_4$-alkyl, and 1 to 1000 ppm by weight, based on the total weight of the composition, of at least one ether of the general formula $R^1$—O—$R^1$.

The invention further provides a composition comprising diisononyl cyclohexane-1,2-dicarboxylate and 10 to 1000 ppm by weight, based on the total weight of the composition, of diisononyl ether.

The invention further provides for the use of the cyclohexanepolycarboxylic ester composition as defined above as plasticizer, preferably as plasticizer for polyvinylchloride.

The invention further provides for use of the cyclohexanepolycarboxylic ester composition as defined above in products intended for human contact, preferably in children's toys, food packaging or in medical articles.

The figures and examples which follow are used to elucidate the invention without restricting it in any way.

DESCRIPTION OF FIGURES

The invention is elucidated in detail hereinafter with reference to FIGS. 1 to 3, but without restricting the invention to the embodiments shown therein.

The following reference signs are used in the figures:
- A stripping section
- B vapor condenser
- D distillation column
- K condenser
- R rectification column
- S phase separation vessel
- V rectifying section
- 1 bottom product (ester)
- 2 steam-containing gas stream (steam)
- 3 feed (crude ester with alcohol, ether, water)
- 4 vapor
- 5 vapor condensate
- 6 aqueous phase
- 7 organic phase (ether, alcohol)
- 8 reflux of organic phase (ether, alcohol)
- 8' reflux of alcohol condensate
- 9 discharge stream of organic phase (ether, alcohol)
- 9' discharge stream of ether
- 10 substream of organic phase
- 11 alcohol-containing gas phase
- 12 alcohol condensate
- 13 condensate reflux
- 14 draw of alcohol condensate

FIG. 1 shows an embodiment of the process of the invention. In a rectification column R, a crude ester as feed 3 is fed in between stripping section A and rectifying section V. The crude ester consists essentially of one or more benzenepolycarboxylic ester(s), $C_4$-$C_{12}$ monoalkanol(s), di-($C_4$-$C_{12}$-alkyl) ether(s) and water. In the stripping section A, a steam-containing gas stream 2 (also referred to hereinafter as steam) is fed in in countercurrent from above the column bottom. Bottom product 1 is drawn off in the column bottom. The bottom product 1 consists essentially of benzenepolycarboxylic ester with a depleted proportion of di-($C_4$-$C_{12}$-alkyl) ether, $C_4$-$C_{12}$ monoalkanol and water compared to the feed. The steam 2 flows through the stripping section A and then the rectifying section V, with passage of alcohol, ether and water from the feed 3 into the vapor phase 2. Vapor 4 is drawn off at the top of the column. The vapor 4 is a mixture comprising steam, di-($C_4$-$C_{12}$-alkyl) ether and $C_4$-$C_{12}$ monoalkanol, and small amounts of benzenepolycarboxylic ester and further components may also be present. The vapor 4 is at least partly condensed in a vapor condenser B and fed as vapor condensate 5 to a phase separation vessel S. In the phase separation vessel S, an aqueous phase 6 comprising essentially water is drawn off in the lower region. Above that, an organic phase 7 comprising essentially di-($C_4$-$C_{12}$-alkyl) ether and $C_4$-$C_{12}$ monoalkanol is drawn off. The organic phase 7 drawn off from the phase separation vessel S is divided into a discharge stream 9 and a condensate reflux stream 8. The condensate reflux stream 8 is fed to the top of the rectification column R above the rectifying section V, such that it is guided in countercurrent to the steam 2.

The aqueous phase 6 drawn off from the phase separation vessel S can suitably be disposed of or optionally recycled into the workup process. The discharge stream 9 may suitably be disposed of or sent to a suitable use.

Figure 2:
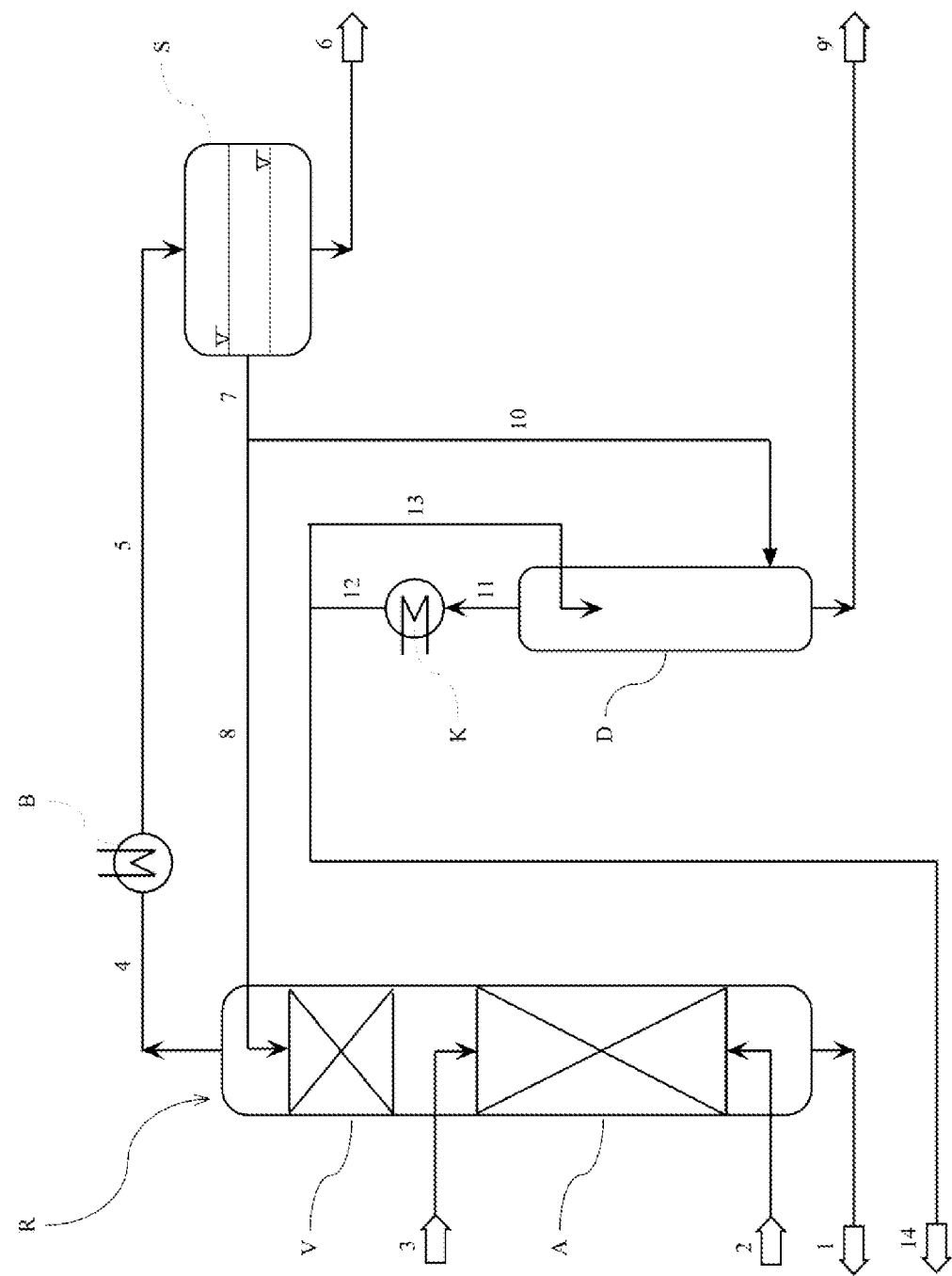
FIG. 2 shows a further preferred embodiment of the process of the invention with an additional distillation column for removal of the vapor condensate.

FIG. 2 shows a further embodiment of the process of the invention. In the rectification column R, the crude ester as feed 3 is fed in between stripping section A and rectifying section V. In the stripping section A, steam 2 is fed in in countercurrent from above the column bottom. The bottom product 1 is drawn off in the column bottom. The steam 2 flows through the stripping section A and then the rectifying section V, with passage of alcohol, ether and water from the feed 3 into the vapor phase. The vapor 4 is drawn off at the top of the column. The vapor 4 is at least partly condensed in a vapor condenser B and fed as vapor condensate 5 to a phase separation vessel S. In the phase separation vessel S, the aqueous phase 6 is drawn off in the lower region. The aqueous phase 6 drawn off from the phase separation vessel S can suitably be disposed of or optionally recycled into the workup process.

In the phase separation vessel S, the organic phase 7 is drawn off via the aqueous phase 6. The organic phase 7 is divided into a reflux stream 8 and a substream 10. The reflux stream 8 is fed to the top of the rectification column R above the rectifying section V, such that it is guided in countercurrent to the steam 2.

The substream 10 is sent to a distillation column D above the bottom. In the bottom of the distillation column D, a discharge stream 9' comprising essentially di-($C_4$-$C_{12}$-alkyl) ether, $C_4$-$C_{12}$ monoalcohol and/or benzenepolycarboxylic ester is drawn off. The discharge stream 9' may suitably be disposed of or sent to a suitable use.

At the top of the distillation column D, an alcohol-containing gas phase is drawn off and at least partly condensed in a condenser K. The alcohol-containing gas phase may, as well as $C_4$-$C_{12}$ monoalkanol, comprise small amounts of water and di-($C_4$-$C_{12}$-alkyl) ether. A portion of the alcohol condensate 12 obtained is recycled as condensate reflux stream 13 to the top of the distillation column D. The remaining alcohol condensate is discharged as condensate draw stream 14 and may be partly or fully recycled into the esterification of the benzenepolycarboxylic acid with the at least one $C_4$-$C_{12}$ monoalkanol.

Figure 3:
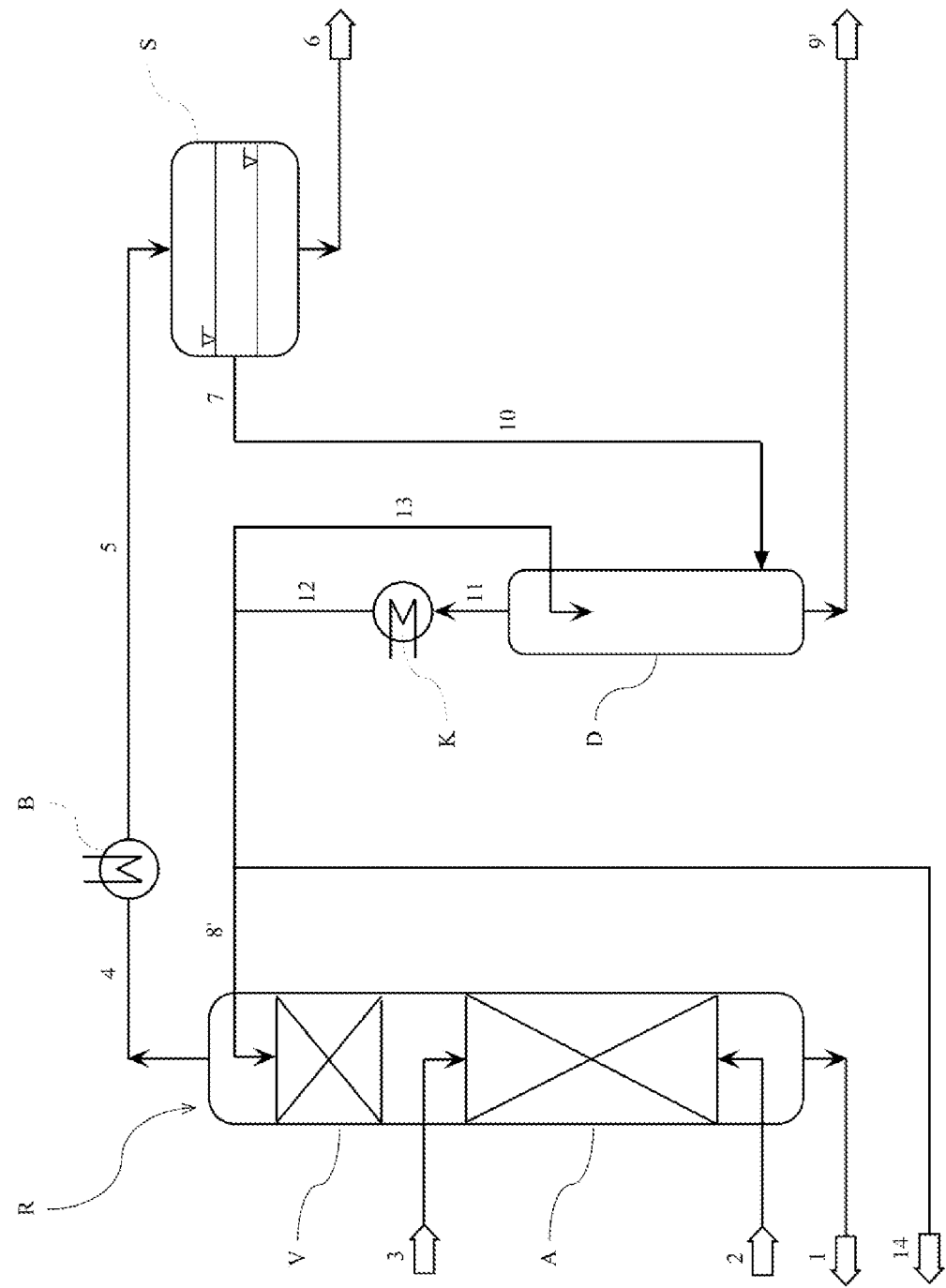
FIG. 3 shows a likewise preferred embodiment of the process of the invention with an additional distillation column for separation of the vapor condensate in an alternative mode of connection to the embodiment shown in FIG. 2.

FIG. 3 shows a further embodiment of the process of the invention. This is an alternative mode of connection to the variant shown in FIG. 2 with distillative separation of the organic phase. In the rectification column R, the crude ester as feed 3 is fed in between stripping section A and rectifying section V. In the stripping section A, steam 2 is fed in in countercurrent from above the column bottom. The bottom product 1 is drawn off in the column bottom. The steam 2 flows through the stripping section A and then the rectifying section V, with passage of alcohol, ether and water from the feed 3 into the vapor phase. The vapor 4 is drawn off at the top of the column. The vapor 4 is at least partly condensed in a vapor condenser B and fed as vapor condensate 5 to a phase separation vessel S. In the phase separation vessel S, the aqueous phase 6 is drawn off in the lower region. The aqueous phase 6 drawn off from the phase separation vessel S can suitably be disposed of or optionally recycled into the workup process.

In the phase separation vessel S, the organic phase 7 is drawn off via the aqueous phase 6. The organic phase 7 is sent to a distillation column D above the bottom. In the bottom of the distillation column D, a discharge stream 9' comprising essentially di-($C_4$-$C_{12}$-alkyl) ether and possibly additions of water, $C_4$-$C_{12}$ monoalcohol and/or benzenepolycarboxylic ester is drawn off. The discharge stream 9' may suitably be disposed of or sent to a suitable use.

At the top of the distillation column D, an alcohol-containing gas phase 11 is drawn off and at least partly condensed in a condenser K. The alcohol-containing gas phase may, as well as $C_4$-$C_{12}$ monoalkanol, comprise small amounts of water and di-($C_4$-$C_{12}$-alkyl) ether. A portion of the alcohol condensate 12 obtained is recycled as condensate reflux stream 13 to the top of the distillation column D. A further portion of the remaining alcohol condensate 12 is fed as reflux stream 8' to the top of the rectification column R above the rectifying section V, such that it is guided in countercurrent to the steam 2. The remaining portion of the alcohol condensate 12 is discharged as condensate draw stream 14 and may be partly or fully recycled into the esterification of the benzenepolycarboxylic acid with the at least one $C_4$-$C_{12}$ monoalkanol.

EXAMPLES

Example 1

Influence of Inlet Temperature of the Crude Ester into the Stripping Column

Figure 1:
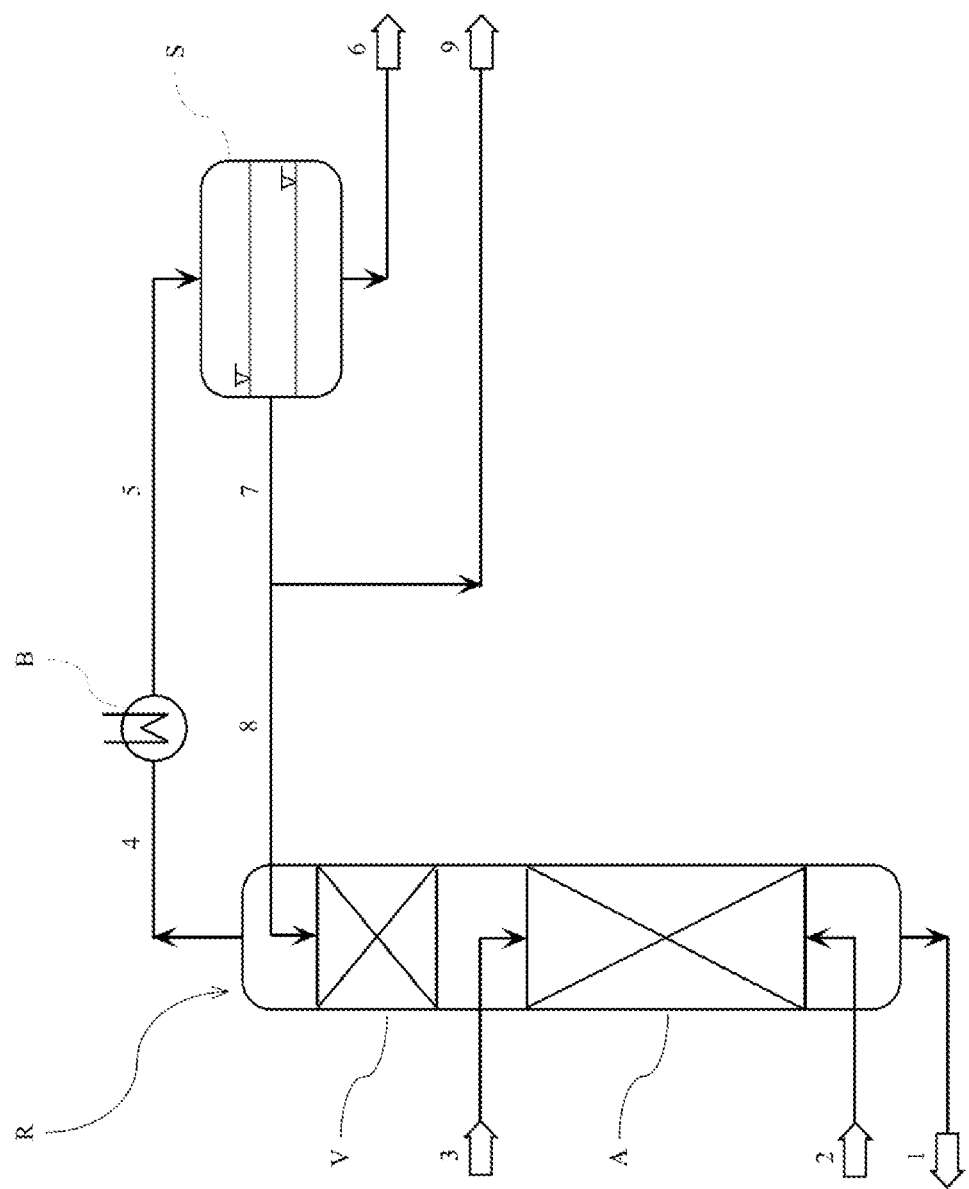
FIG. 1 shows a preferred embodiment of the process of the invention with a vapor phase separation vessel.
Figure 4:
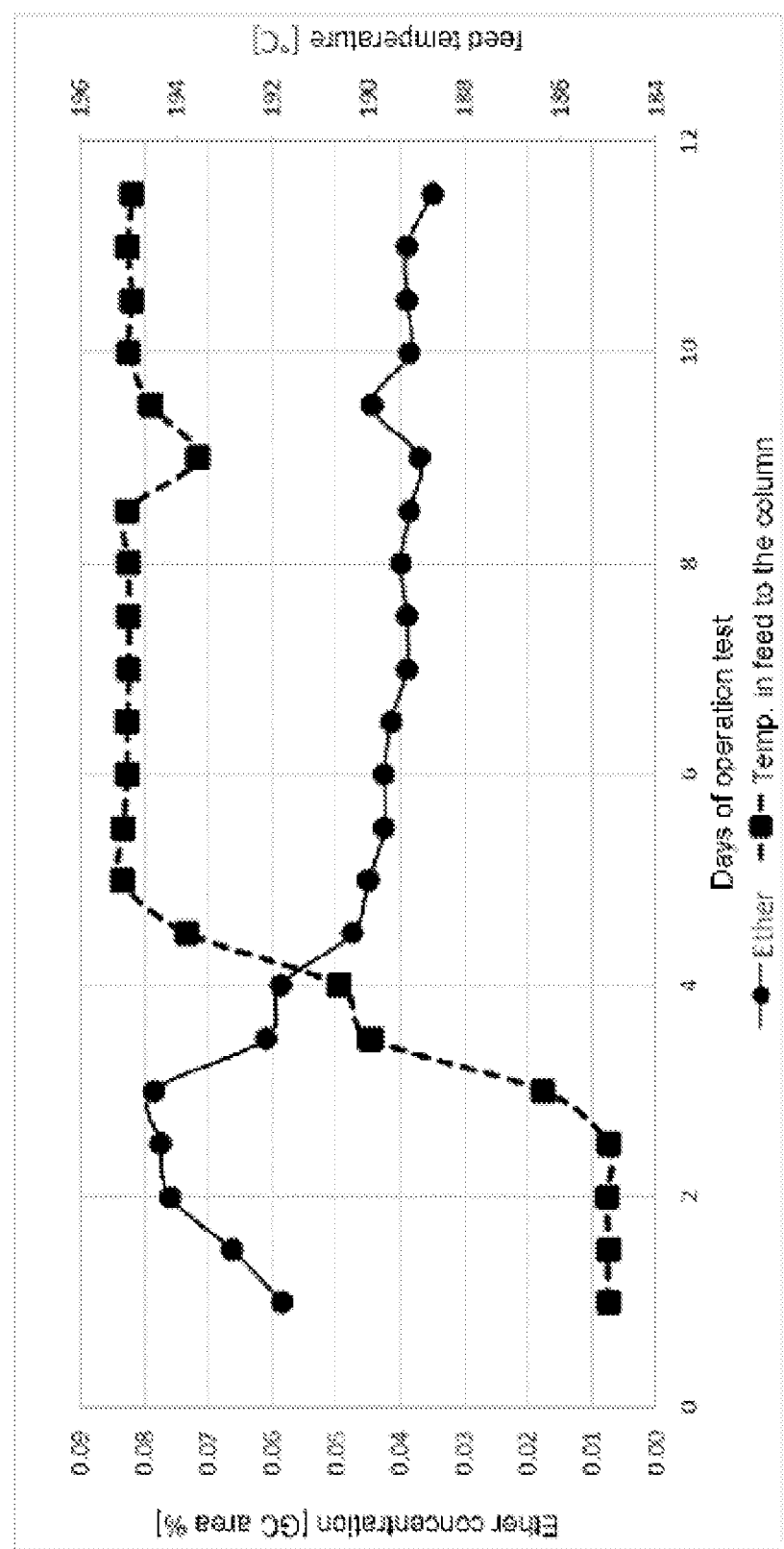
FIG. 4 shows the diisononyl ether content in the bottom product depending on the inlet temperature of the crude ester.

Into a rectification column (stripping column) according to FIG. 1 is fed, between the stripping section and rectifying section, a crude diisononyl phthalate as feed at a feed rate of 13 000 kg/h. The crude ester further comprises diisononanol, diisononyl ether and water. The stripping column is operated at a pressure of 50 mbar absolute. Above the column bottom, in countercurrent to the crude ester, steam is fed in at 4 bar and the crude ester is stripped with 3% by weight of steam, based on crude ester. The inlet temperature of the crude ester into the column is at first left constant at 185° C. and then increased in multiple steps to 195° C. At the top of the column, the vapor is drawn off, condensed and discharged. There is no recycling of condensed vapor to the top of the column. The diisononyl ether content in the bottom product is determined. FIG. 4 shows the diisononyl ether content in the bottom product depending on the inlet temperature of the crude ester. It shows that the diisononyl ether content in the bottom product can be distinctly reduced from about 600-800 ppm by weight to about 400 ppm by weight by increasing the inlet temperature of the crude ester into the column.

Example 2

Hydrogenation of Diisononyl Phthalate (DINP) to Diisononyl cyclohexane-1,2-dicarboxylate (DINCH)

The raw material used for the inventive hydrogenation 1 was diisononyl phthalate from a batch from example 1 in which the diisononyl ether content was 500 ppm by weight owing to the elevated stripping temperature. The hydrogenation V1 is a comparative experiment wherein the raw material used was diisononyl phthalate from a batch from example 1 wherein the ether concentration was 590 ppm by weight owing to the lower stripping temperature. The hydrogenation catalyst used in all experiments was a ruthenium catalyst on a macro/mesoporous alumina support prepared according to the catalyst preparation example on page 7 lines 36-47 of DE 19624485 A1. The ruthenium content of the catalyst was 0.5%.

The hydrogenations were conducted in a cascade of 3 reactors (internal diameter 1 m, length 20 m). The first reactor was operated as the main reactor with circulation, i.e. the discharge from the first reactor was partly recycled to the inlet of the first reactor. The last 2 reactors were operated as postreactors in straight pass. The reactors were each charged with 9000 kg of catalyst.

The hydrogenation was conducted with pure hydrogen. The feed was chosen such that the catalyst hourly space velocity in the main reactor (kg(diisononyl phthalate)/L (catalyst)·h) reaches the value specified in the table below. The recycle rate was chosen such that the superficial velocity in the main reactor has the values specified in table 1. The hydrogen was supplied in a pressure-regulated manner at the pressure specified in table 1. The reaction temperatures are likewise specified in table 1.

TABLE 1

Hydrogenation experiments

| No. | Main reactor | | | | Postreactor 1 | | | Postreactor 2 | | | Pressure Reactors [bar] |
|---|---|---|---|---|---|---|---|---|---|---|---|
| | A | B | C | D | A | B | C | A | B | C | |
| V1 | 9.8 | 160 | 123 | 10 | 3.0 | 52 | 138 | 1.3 | 23 | 117 | 250 |
| 1 | 9.8 | 160 | 123 | 10 | 3.0 | 52 | 138 | 1.3 | 23 | 117 | 250 |

A) catalyst hourly space velocity: kg(diisononyl phthalate)/(L(catalyst) h)
B) superficial velocity: $m^3$(diisononyl phthalate)/($m^2$(reactor cross section) (h))
C) temperature [° C.]
D) recycle rate: kg of hydrogenation product recycled/kg diisononyl phthalate The analysis of the diisononyl phthalate used and of the diisononyl cyclohexane-1,2-dicarboxylate obtained was effected by the following GC method:
Column: DB-1 30 m (100% dimethylpolysiloxane), ID 0.32 mm, FD 0.25 μm
Detector: flame ionization detector (FID)
Temperature program: starting temperature 80° C., hold time 1 min, heating at 5° C./min to 300° C., hold time 15 min
Injection volume: 0.2 μL
Inlet temperature: 300° C.
Detector temperature: 320° C.
Retention times:
Isononanol: 4-9.5 min
Diisononyl cyclohexane-1,2-dicarboxylate (DINCH): 32.5-43 min
Tables 2a and 2b: Results of the Hydrogenation Experiments

| No. | Diisononyl phthalate (DINP) Diisononyl ether [% by wt.][a] | Diisononyl cyclohexane-1,2-dicarboxylate (DINCH) | | Total of others [% by wt.] |
|---|---|---|---|---|
| | | DINCH [% by wt.] | Diisononyl ether [% by wt.] | |
| V1 | 0.059 | 99.84 | 0.113 | 0.047 |
| 1 | 0.050 | 99.82 | 0.082 | 0.098 |

[a]determined as GC area %

| No. | Diisononyl cyclohexane-1,2-dicarboxylate (DINCH) | | | | Residual aromatics (DINP) [ppm] |
|---|---|---|---|---|---|
| | Water [% by wt.] | Acid number [mg KOH/g] | Pt/Co color number | | |
| V1 | 0.019 | 0.03 | 3 | | 4 |
| 1 | 0.013 | 0.01 | 4 | | 2 |

The experiments show that, by the process of the invention, a diisononyl phthalate having a low content of diisononyl ether affords, through hydrogenation using a ruthenium catalyst on a macro/mesoporous alumina support, a diisononyl cyclohexane-1,2-dicarboxylate (DINCH) having a content of diisononyl ethers of not more than 0.1% by weight. The experiments likewise show that a diisononyl phthalate having an elevated content of diisononyl ethers, by means of the hydrogenation process of the invention, affords a diisononyl cyclohexane-1,2-dicarboxylate (DINCH) having an undesirably high content of diisononyl ethers of more than 0.1% by weight.

Example 3

Into the stripping column according to FIG. 1 is continuously fed a crude diisononyl phthalate as feed at a feed rate of 20 000 kg/h. The inlet temperature of the crude ester into the column is 185° C. The stripping column is operated at 50 mbar absolute. Above the column bottom, in countercurrent to the crude ester, steam is fed in at 4 bar and the crude ester is stripped with 3% by weight of steam, based on crude ester. The condensed vapors are separated in a phase separation vessel into an aqueous phase and an organic phase. The aqueous phase is disposed of in each case. Until day 8, the organic phase is also drawn off completely from the phase separation vessel as discharge stream. The continuous discharge of the condensed vapor reduces the concentration of diisononyl ether in the bottom product from 310 ppm by weight to 250 ppm by weight within 8 days. Correspondingly, there is also a decrease in the concentration of diisononyl ether in the organic phase. By contrast, the concentration of product of value (DINP) in the organic phase and the total amount of vapor (distillate) remain unchanged.

The implementation of a reflux stream of 200 kg/h of organic phase on days 28 and 46 and recycling of the remaining organic phase into the ester synthesis distinctly reduces the concentration of DINP in the organic phase. The total amount of vapor (distillate) also declines; there is simultaneously a slight increase in the amount of diisononyl ether in the organic phase and in the stripped bottom product. This behavior is reproducible.

TABLE 3

Results of the operating experiment

| Day | Reflux rate to top of column [kg/h] | Vapor discharged or back to top and into synthesis | Distillate rate [kg/h] | Low boilers[a] % by wt. | Ethers % by wt. | High boilers % by wt. | Isononanol % by wt. | DINP % by wt. | Ether in the product ppm by wt. |
|---|---|---|---|---|---|---|---|---|---|
| 0 | 0 | Disposal | 171 | 1.4 | 3.3 | 0 | 71 | 23 | 310 |
| 1 | 0 | Disposal | 182 | 1.2 | 3 | 0 | 76 | 19 | 310 |
| 4 | 0 | Disposal | 183 | 0.9 | 2.56 | 0 | 77 | 19 | 280 |
| 5 | 0 | Disposal | 179 | 0.8 | 2.4 | 0 | 72 | 23 | 260 |
| 8 | 0 | Disposal | 179 | 0.9 | 2.24 | 0 | 77 | 20 | 250 |
| 28 | 200 | Synthesis | 165 | 1.1 | 4.3 | 0 | 87.5 | 5.8 | 350 |
| 42 | 0 | Disposal | 190 | 1 | 2.2 | 0 | 72.5 | 23.8 | 200 |
| 44 | 0 | Disposal | 188 | 1 | 2.2 | 0 | 72.4 | 23.8 | 300 |
| 46 | 200 | Synthesis | 150 | 1 | 3.6 | 0 | 89.5 | 4.8 | 320 |
| 49 | 0 | Disposal | 182 | 1.2 | 3.7 | 0 | 89.5 | 4.6 | 370 |
| 50 | 0 | Disposal | 200 | 0.9 | 2.5 | 0 | 73 | 22.6 | 280 |

[a] primarily C$_9$-alkene

Example 4

Figure 5:
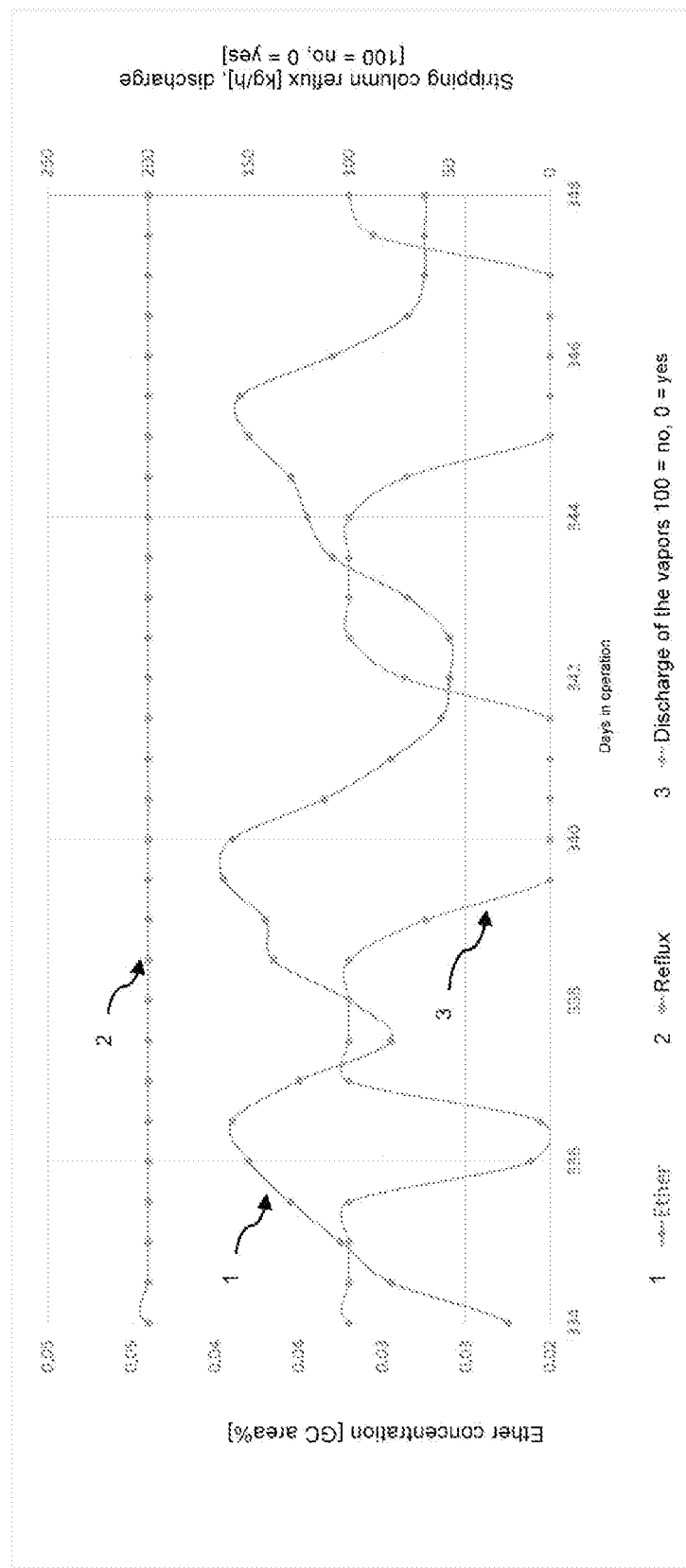
FIG. 5 shows an embodiment according to variant 2 of the process of the invention. Curve 2 shows that the organic phase obtained by phase separation from the condensed vapor is run at a constant rate (200 kg/h) as recycle stream to the top of the stripping column. Curve 3 shows the intervals in which the remaining amount of the organic phase is recycled into the ester synthesis or discharged. Curve 1 shows the diisononyl ether content in the bottom product.

As described in example 3, a crude diisononyl phthalate is treated in a stripping column according to FIG. 1. A portion of the organic phase obtained by phase separation from the condensed vapor is run as recycle stream to the top of the stripping column (200 kg/h). The remaining amount of the organic phase is alternately recycled into the ester synthesis or discharged. By this method, the concentration of diisononyl ether in the bottom product can be controlled and kept at the desired content of 300 to 400 ppm by weight. It is thus possible to achieve low ether contents in the product and simultaneously to distinctly reduce the proportion of product of value (DINP) in the discharged vapor stream (see FIG. 5).

Example 5

Separation of Ether and Alcohol on the Laboratory Scale

An oil-heated 2 L jacketed vessel with stirrer and with a distillation column on top (diameter 30 mm, length 3.05 m, filled with 1.75 m of Sulzer DX and 1.3 m of Montz A3-1000 structured packing) was used. The column has a tops condenser, by means of which a defined reflux can be established, and which enables distillation under reduced pressure.

1.3 kg of a mixture that comprised 5.36% by weight of water, 1.15% by weight of low boilers (nonenes, phthalic anhydride, phthalide, benzoic acid, nonyl benzoate), 84.5% by weight of isononanol, 3.5% by weight of diisononyl ether, 1.04% by weight of further medium boilers and 4.4% by weight of DINP was initially charged in the pot.

The distillation was conducted under a reduced pressure of 100 mbar; the supply of heat to the vessel and hence the distillation temperature was controlled via the pressure drop across the column. The reflux ratio was set to a value of 2, and the pressure drop across the column to 2.5 mbar.

The components of the mixture were distilled off successively in accordance with their boiling temperature. Samples of the distillate, each of 20 to 30 g, were taken over the duration of the experiment. A total of 23 samples were taken and analyzed by means of gas chromatography. The composition of the samples is shown in table 4. On attainment of a bottom temperature of 180° C., the distillation was ended. The residue in the vessel was analyzed by means of gas chromatography. Through the distillation, it is possible to concentrate the DINP/ether mixture from about 7.9% to about 84%. Distillates isolated were isononanol/water mixtures having an alcohol concentration of more than 95%. Such an alcohol can be used for synthesis of DINP.

TABLE 4

Composition of the distillate samples and of the bottoms remaining at the end of the distillation

| Distillate sample | Water [% by wt.] | Low boilers [% by wt.] | Isononanol [% by wt.] | Medium boilers 1[a] [% by wt.] | Diisononyl ether [% by wt.] | Medium boilers 2[b] [% by wt.] | DINP [% by wt.] |
|---|---|---|---|---|---|---|---|
| 1 | 88.48 | 8.59 | 2.35 | 0.00 | 0.00 | 0.00 | 0.00 |
| 2 | 96.62 | 1.79 | 0.59 | 0.00 | 0.00 | 0.00 | 1.00 |
| 3 | 99.90 | 0.07 | 0.02 | 0.00 | 0.00 | 0.00 | 0.01 |
| 4 | 46.39 | 22.36 | 31.87 | 0.04 | 0.00 | 0.00 | 0.30 |
| 5 | 1.14 | 15.01 | 83.77 | 0.07 | 0.00 | 0.00 | 0.01 |
| 6 | 1.83 | 3.72 | 94.11 | 0.17 | 0.00 | 0.00 | 0.16 |
| 7 | 1.19 | 1.39 | 97.17 | 0.16 | 0.00 | 0.00 | 0.10 |
| 8 | 1.42 | 0.46 | 97.77 | 0.15 | 0.00 | 0.00 | 0.21 |
| 9 | 0.89 | 0.05 | 98.38 | 0.21 | 0.00 | 0.01 | 0.46 |
| 10 | 0.78 | 0.04 | 98.53 | 0.65 | 0.00 | 0.00 | 0.00 |
| 11 | 1.72 | 0.03 | 96.31 | 1.94 | 0.00 | 0.00 | 0.00 |
| 12 | 1.00 | 0.02 | 96.62 | 2.28 | 0.00 | 0.00 | 0.00 |
| 13 | 0.40 | 0.01 | 96.91 | 2.69 | 0.00 | 0.00 | 0.00 |
| 14 | 0.14 | 0.01 | 96.84 | 3.01 | 0.00 | 0.00 | 0.00 |
| 15 | 0.06 | 0.00 | 99.26 | 0.68 | 0.00 | 0.00 | 0.00 |
| 16 | 0.03 | 0.00 | 99.46 | 0.50 | 0.00 | 0.00 | 0.00 |
| 17 | 0.03 | 0.00 | 99.59 | 0.39 | 0.00 | 0.00 | 0.00 |
| 18 | 0.03 | 0.00 | 99.64 | 0.33 | 0.00 | 0.00 | 0.00 |

TABLE 4-continued

Composition of the distillate samples and of the bottoms remaining at the end of the distillation

| Distillate sample | Water [% by wt.] | Low boilers [% by wt.] | Isononanol [% by wt.] | Medium boilers 1[a] [% by wt.] | Diisononyl ether [% by wt.] | Medium boilers 2[b] [% by wt.] | DINP [% by wt.] |
|---|---|---|---|---|---|---|---|
| 19 | 0.04 | 0.01 | 99.40 | 0.55 | 0.00 | 0.00 | 0.01 |
| 20 | 0.04 | 0.00 | 99.69 | 0.19 | 0.00 | 0.00 | 0.06 |
| 21 | 0.02 | 0.00 | 99.86 | 0.11 | 0.00 | 0.00 | 0.00 |
| 22 | 0.02 | 0.00 | 99.89 | 0.08 | 0.00 | 0.00 | 0.02 |
| 23 | 0.04 | 0.01 | 99.86 | 0.09 | 0.00 | 0.00 | 0.01 |
| Bottoms | 0.01 | 0 | 6.25 | 8.44 | 34.92 | 0.61 | 49.75 |

[a] lower-boiling than diisononyl ether
[b] higher-boiling than diisononyl ether

The invention claimed is:

1. A process for workup of a crude ester from the esterification of a benzenepolycarboxylic acid with at least one $C_4$-$C_{12}$ monoalkanol, wherein the crude ester additionally comprises
   at least one di-($C_4$-$C_{12}$-alkyl) ether from the etherification of the at least one $C_4$-$C_{12}$ monoalkanol,
   the at least one $C_4$-$C_{12}$ monoalkanol, and
   optionally water,
the process comprising subjecting the crude ester to a thermal purification in at least one mass transfer apparatus by introducing a steam-containing gas stream in the region of the bottom of the mass transfer apparatus to obtain a bottom product enriched in the at least one benzenepolycarboxylic ester and depleted of the at least one di-($C_4$-$C_{12}$-alkyl) ether and a vapor enriched in the at least one di-($C_4$-$C_{12}$-alkyl) ether;
at least partly condensing the vapor into a condensate, and separating the condensate into an aqueous phase and an organic phase comprising di-($C_4$-$C_{12}$-alkyl) ether and $C_4$-$C_{12}$ monoalkanol, recycling a portion of the organic phase as a reflux stream into the thermal purification of the crude ester, and discharging another portion of the organic phase.

2. The process according to claim 1, wherein the crude ester used for workup comprises
   91% to 99.8% by weight of at least one ester of a benzenepolycarboxylic acid with at least one $C_4$-$C_{12}$ monoalkanol,
   0.05% to 1% by weight of at least one di-($C_4$-$C_{12}$-alkyl) ether,
   0.1% to 5% by weight of at least one $C_4$-$C_{12}$ monoalkanol, and
   0.05% to 3% by weight of water.

3. The process according to claim 1, wherein thermal purification is accomplished using at least one column having
   a side feed for the crude ester,
   a rectifying section above the feed point for the crude ester,
   a reflux feed for the reflux stream located above the rectifying section, and
   a feed for the steam-containing gas stream in the region of the bottom of the column.

4. The process according to claim 3, wherein the rectifying section above the feed point for the crude ester has 0 to 10 theoretical plates.

5. The process according to claim 1, further comprising recycling a third portion of the organic phase into the esterification of the benzenepolycarboxylic acid with the at least one $C_4$-$C_{12}$ monoalkanol.

6. The process according to claim 1, wherein the discharge of a portion of the organic phase is batchwise or continuous.

7. The process according to claim 5, further comprising controlling the content in the bottom product of di-($C_4$-$C_{12}$-alkyl) ether by implementing control interventions on at least one of the following manipulated variables:
   the mass flow of the reflux stream of the organic phase,
   the mass flow of the organic phase recycled into the esterification, and
   the mass flow of the organic phase discharged.

8. The process according to claim 7, in which
   a target value for the content in the bottom product of di-($C_4$-$C_{12}$-alkyl) ether and an upper and lower limit for the variance of the actual value from the target value are fixed,
   the actual value of the content in the bottom product of di-($C_4$-$C_{12}$-alkyl) ether is determined,
   on attainment of the upper limit for the variance of the actual value from the target value, control interventions are implemented until the content in the bottom product of di-($C_4$-$C_{12}$-alkyl) ether has fallen to the lower limit for the variance of the actual value from the target value.

9. The process according to claim 8, wherein the target value for the content in the bottom product of di-($C_4$-$C_{12}$-alkyl) ether is not more than 1000 ppm by weight.

10. A process for workup of a crude ester from the esterification of a benzenepolycarboxylic acid with at least one $C_4$-$C_{12}$ monoalkanol, wherein the crude ester additionally comprises
   at least one di-($C_4$-$C_{12}$-alkyl) ether from the etherification of the at least one $C_4$-$C_{12}$ monoalkanol,
   the at least one $C_4$-$C_{12}$ monoalkanol, and
   optionally water,
the process comprising subjecting the crude ester-to a thermal purification in at least one mass transfer apparatus by introducing a steam-containing gas stream in the region of the bottom of the mass transfer apparatus to obtain a bottom product enriched in the at least one benzenepolycarboxylic ester and depleted of the at least one di-($C_4$-$C_{12}$-alkyl) ether and a vapor enriched in the at least one di-($C_4$-$C_{12}$-alkyl) ether;
wherein the vapor is at least partly condensed, the condensate is separated into an aqueous phase and an organic phase comprising di-($C_4$-$C_{12}$-alkyl) ether and $C_4$-$C_{12}$ monoalkanol, at least a portion of the organic phase is subjected to a separation into a di-($C_4$-$C_{12}$-alkyl) ether-enriched fraction and a $C_4$-$C_{12}$ monoalkanol-enriched fraction, and the di-($C_4$-$C_{12}$-alkyl) ether-enriched fraction is partly or fully discharged.

11. The process according to claim 10, wherein a portion of the organic phase is subjected to a separation into a di-($C_4$-$C_{12}$-alkyl) ether-enriched fraction and a $C_4$-$C_{12}$ monoalkanol-enriched fraction, and another portion of the organic phase is recycled as a reflux stream into the thermal purification of the crude ester.

12. The process according to claim 10, further comprising partly or fully recycling the $C_4$-$C_{12}$ monoalkanol-enriched fraction as a reflux stream into the thermal purification of the crude ester.

13. The process according to claim 10, wherein the $C_4$-$C_{12}$ monoalkanol-enriched fraction is partly or fully recycled into the esterification of the benzenepolycarboxylic acid with the at least one $C_4$-$C_{12}$ monoalkanol.

14. A process for preparing a cyclohexanepolycarboxylic ester, comprising
  i) providing a crude ester from the esterification of a benzenepolycarboxylic acid with at least one $C_4$-$C_{12}$ monoalkanol,
  ii) subjecting the crude ester provided in step i) to a workup as defined in claim 1 to obtain a benzenepolycarboxylic ester depleted of di-($C_4$-$C_{12}$-alkyl) ethers compared to the crude ester, and
  iii) subjecting the benzenepolycarboxylic ester depleted of di-($C_4$-$C_{12}$-alkyl) ethers which is obtained in step ii) to a hydrogenation with a hydrogen-containing gas in the presence of a hydrogenation catalyst.

15. The process according to claim 14, wherein the hydrogenation catalyst used in step iii) is selected from
  catalysts comprising, as an active metal, at least one metal from transition group VIII of the Periodic Table of the Elements applied to a porous support, where 5% to 50% of the pore volume of the support is formed by macropores having a pore diameter in the range from 50 nm to 10 000 nm and 50% to 95% of the pore volume of the support is formed by mesopores having a pore diameter in the range from 2 to less than 50 nm, wherein the sum total of the pore volumes adds up to 100%, and
  eggshell catalysts comprising an active metal selected from ruthenium, rhodium, palladium, platinum and mixtures thereof, applied to a support material comprising porous silicon dioxide, where the pore volume of the support material is 0.6 to 1.0 mL/g, determined by Hg porosimetry, the BET surface area is 280 to 500 $m^2$/g, and at least 90% of the pores present have a diameter of 6 to 12 nm.

16. The process according to claim 3, wherein the rectifying section above the feed point for the crude ester has 0 to 5 theoretical plates.

17. The process according to claim 3, wherein the rectifying section above the feed point for the crude ester has 0 to 2 theoretical plates.

18. The process according to claim 8, wherein the target value for the content in the bottom product of di-($C_4$-$C_{12}$-alkyl) ether is not more than 800 ppm by weight.

19. The process according to claim 8, wherein the target value for the content in the bottom product of di-($C_4$-$C_{12}$-alkyl) ether is not more than 600 ppm by weight.

20. The process according to claim 8, wherein the target value for the content in the bottom product of di-($C_4$-$C_{12}$-alkyl) ether is not more than 500 ppm by weight.

21. The process according to claim 10, wherein the crude ester used for workup comprises
  91% to 99.8% by weight of at least one ester of a benzenepolycarboxylic acid with at least one $C_4$-$C_{12}$ monoalkanol,
  0.05% to 1% by weight of at least one di-($C_4$-$C_{12}$-alkyl) ether,
  0.1% to 5% by weight of at least one $C_4$-$C_{12}$ monoalkanol, and
  0.05% to 3% by weight of water.

22. The process according to claim 11, wherein thermal purification is accomplished using at least one column having
  a side feed for the crude ester,
  a rectifying section above the feed point for the crude ester,
  a reflux feed for the reflux stream located above the rectifying section, and
  a feed for the steam-containing gas stream in the region of the bottom of the column.

23. The process according to claim 22, wherein the rectifying section above the feed point for the crude ester has 0 to 10 theoretical plates.

24. A process for preparing a cyclohexanepolycarboxylic ester, comprising
  i) providing a crude ester from the esterification of a benzenepolycarboxylic acid with at least one $C_4$-$C_{12}$ monoalkanol,
  ii) subjecting the crude ester provided in step i) to a workup as defined in claim 10 to obtain a benzenepolycarboxylic ester depleted of di-($C_4$-$C_{12}$-alkyl) ethers compared to the crude ester, and
  iii) subjecting the benzenepolycarboxylic ester depleted of di-($C_4$-$C_{12}$-alkyl) ethers which is obtained in step ii) to a hydrogenation with a hydrogen-containing gas in the presence of a hydrogenation catalyst.

25. The process according to claim 24, wherein the hydrogenation catalyst used in step iii) is selected from
  catalysts comprising, as an active metal, at least one metal from transition group VIII of the Periodic Table of the Elements applied to a porous support, where 5% to 50% of the pore volume of the support is formed by macropores having a pore diameter in the range from 50 nm to 10 000 nm and 50% to 95% of the pore volume of the support is formed by mesopores having a pore diameter in the range from 2 to less than 50 nm, wherein the sum total of the pore volumes adds up to 100%, and
  eggshell catalysts comprising an active metal selected from ruthenium, rhodium, palladium, platinum and mixtures thereof, applied to a support material comprising porous silicon dioxide, where the pore volume of the support material is 0.6 to 1.0 mL/g, determined by Hg porosimetry, the BET surface area is 280 to 500 $m^2$/g, and at least 90% of the pores present have a diameter of 6 to 12 nm.

* * * * *